(12) United States Patent  (10) Patent No.: US 9,176,743 B2
Simske et al.  (45) Date of Patent: Nov. 3, 2015

(54) FORENSIC AUTHENTICATION IN ELECTRONIC WORKFLOWS

(75) Inventors: Steven J. Simske, Fort Collins, CO (US); Guy Adams, Stroud (GB)

(73) Assignee: Hewlett-Packard Development Company, L.P., Houston, TX (US)

(*) Notice: Subject to any disclaimer, the term of this patent is extended or adjusted under 35 U.S.C. 154(b) by 147 days.

(21) Appl. No.: 13/810,697

(22) PCT Filed: Dec. 20, 2010

(86) PCT No.: PCT/US2010/061215
§ 371 (c)(1),
(2), (4) Date: Jan. 17, 2013

(87) PCT Pub. No.: WO2012/087270
PCT Pub. Date: Jun. 28, 2012

(65) Prior Publication Data
US 2013/0290963 A1  Oct. 31, 2013

(51) Int. Cl.
*G06F 9/46* (2006.01)
*G06F 9/44* (2006.01)
*G06Q 10/10* (2012.01)
*G06Q 10/06* (2012.01)
*G06Q 10/08* (2012.01)
*G06Q 50/18* (2012.01)
*G06Q 50/22* (2012.01)

(52) U.S. Cl.
CPC *G06F 9/44* (2013.01); *G06Q 10/06* (2013.01); *G06Q 10/08* (2013.01); *G06Q 10/10* (2013.01); *G06Q 50/18* (2013.01); *G06Q 50/22* (2013.01)

(58) Field of Classification Search
CPC ....... G06Q 50/18; G06Q 50/22; G06Q 10/08; G06Q 10/10; G06Q 10/06; G06F 9/44
See application file for complete search history.

(56) References Cited

U.S. PATENT DOCUMENTS 6,324,353 B1 * 11/2001 Laussermair et al. .......... 399/16
6,803,861 B2    10/2004 Flick
7,016,687 B1     3/2006 Holland
7,277,601 B2 * 10/2007 Zorab et al. ................... 382/305

(Continued)

FOREIGN PATENT DOCUMENTS

JP       H10-221426 A      8/1998
WO    WO-2004025320 A1   3/2004

OTHER PUBLICATIONS

Klemmer, Scott R et al, "Toolkit Support for Integrating Physical and Digital Interactions" Research paper 2009.

*Primary Examiner* — Van Nguyen
(74) *Attorney, Agent, or Firm* — Pearl, Cohen

(57) ABSTRACT

A system for performing task execution in a workflow includes a processor device, at least one modular device having a digital microscope that is interchangeably coupled to the processor device, a memory device coupled to the processor device comprising instructions that when executed by the processor device execute a software service, a network interface, and an electronic workflow system coupled to the processor device via the network interface. The digital microscope corresponds to at least one particular task of a workflow to authenticate a workflow item using discrepancy detection, and the software service controls operation of the at least one modular device and generates forensic metadata from task information received by the digital microscope of the at least one modular device for the electronic workflow system.

17 Claims, 16 Drawing Sheets

(56) References Cited

U.S. PATENT DOCUMENTS

| | | | |
|---|---|---|---|
| 7,357,300 B2* | 4/2008 | Hull et al. | 235/376 |
| 7,387,249 B2* | 6/2008 | Hudson et al. | 235/462.01 |
| 7,812,935 B2* | 10/2010 | Cowburn et al. | 356/71 |
| 7,895,257 B2* | 2/2011 | Helal et al. | 709/201 |
| 8,572,695 B2* | 10/2013 | Bailloeul et al. | 726/4 |
| 2005/0182757 A1 | 8/2005 | Hull | |
| 2007/0011037 A1 | 1/2007 | Demizu et al. | |
| 2007/0061358 A1 | 3/2007 | Brooks et al. | |
| 2007/0100990 A1 | 5/2007 | Brown et al. | |
| 2007/0115497 A1* | 5/2007 | Cowburn | 358/1.14 |
| 2008/0044096 A1* | 2/2008 | Cowburn et al. | 382/238 |
| 2008/0243902 A1 | 10/2008 | Rong et al. | |
| 2009/0260017 A1 | 10/2009 | Yoshida | |
| 2010/0057628 A1 | 3/2010 | Trinidad et al. | |
| 2010/0070945 A1 | 3/2010 | Tattrie et al. | |

* cited by examiner

FORENSIC AUTHENTICATION IN ELECTRONIC WORKFLOWS

BACKGROUND

Documents and other printed materials may be incorporated into workflows for monitoring, tracking, data gathering etc. A workflow may include a sequence of connected steps and may provide a depiction for a sequence of operations, which may be declared as the "work" or task(s) of a person, a group of persons, an organization, and/or some other functional mechanism.

A workflow may be seen as an abstraction of real work. From the point of view of task management, a workflow may provide a view or glimpse of real work that is occurring or may occur. A workflow may serve also as a virtual representation of actual work. The flow or movement being described in a workflow may refer to a document or printed material (such as a label attached to a product) that is being transferred from one step to another.

Workflow use may be increasing, in part because of factors such as increased use of mobile imaging to connect physical items (like labels and other documents) to electronic (computerized) back-end processes. Additionally, as more tasks incorporate computerized monitoring or tracking features (or become in general more digital/electronic), and as features such as cloud services (Web-based computing resources) become more available to enable collaborative workflows (which may have been previously impractical), the rate of workflow use may further increase. Such an Increase may cause a continually larger percentage of printed material to be intentionally linked in workflows to provide electronic content (e.g. tracking or monitoring data) that may be "on-line" and available in real time.

Labels, packaging, documents, tickets and many other printed items may serve as tokens in electronic workflows. Labels, for example, increasingly "carry" (or are linked to) point-of-sale, consumer/brand interaction, "track and trace" (e.g. logistics for determining current and past locations of property), "ePedigree" (e.g. electronic chain-of-custody), authentication, and/or forensic information that can be examined or "interrogated" by a manufacturer, distributor, retailer, consumer, and/or investigative agent, as part of their interaction with the physical world.

Figure 1:
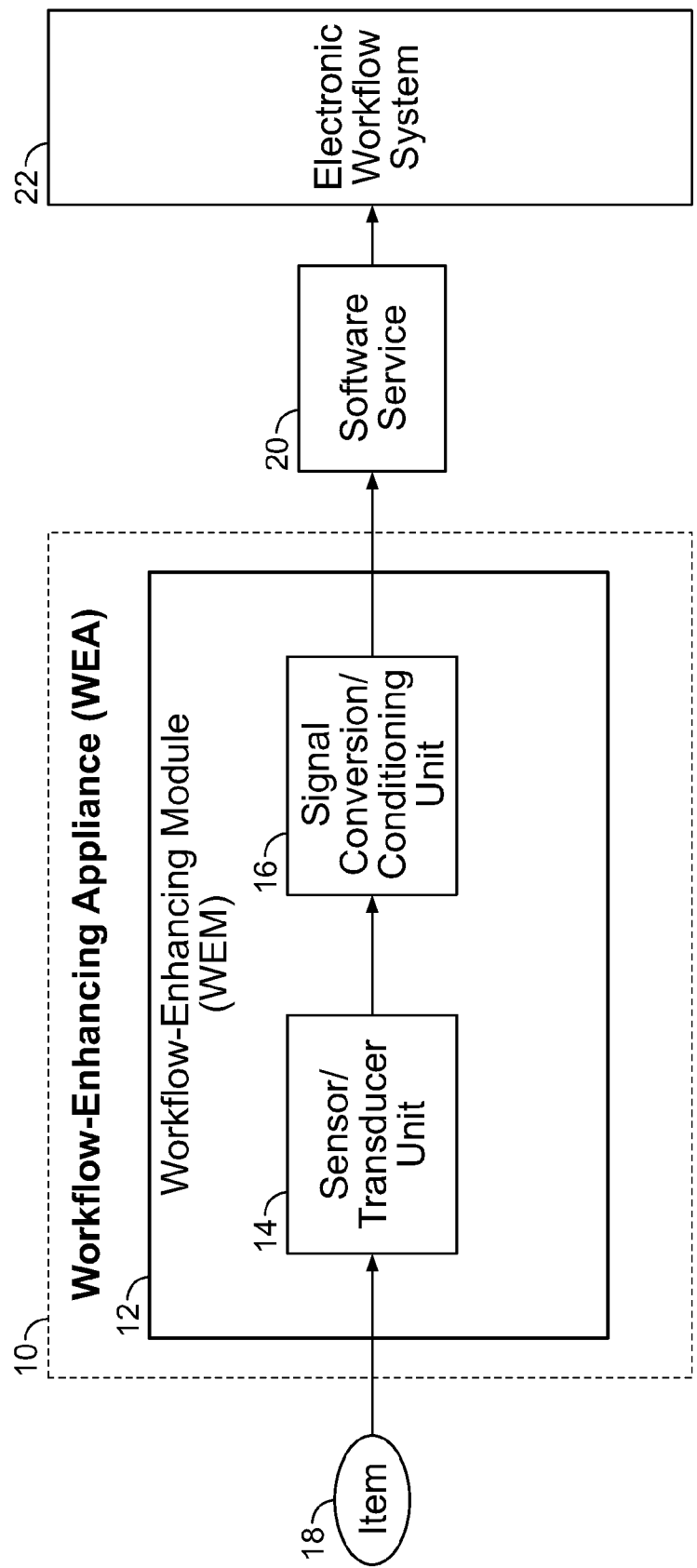
FIG. 1 illustrates a workflow-enhancing appliance in accordance with an embodiment of the invention.

Where considered appropriate, reference numerals may be repeated among the drawings to indicate corresponding or analogous elements. Moreover, some of the blocks depicted in the drawings may be combined into a single function.

DETAILED DESCRIPTION

In the following detailed description, numerous specific details are set forth in order to provide a thorough understanding of different embodiments of the invention. However, it will be understood by those of ordinary skill in the art that embodiments of the present invention may be practiced without these specific details. In other instances, well-known methods, procedures, components, and circuits have not been described in detail so as not to obscure the invention.

An embodiment of the invention may provide a modular, customizable workflow-enhancing appliance (WEA), for performing workflow-related tasks and interfacing with electronic workflows. A WEA may allow, for example, data exchange with an electronic workflow while a user accomplishes a task pertinent to the workflow. An embodiment of the invention may provide a system and method for executing a workflow, using a WEA, and a system and method for modular, customizable workflow execution.

An electronic workflow may be a computer-based system to monitor or enable a set of tasks—for example, tasks for a business, tasks for medical treatment, and/or other process tasks. The term "tasks" as used herein may be an activity or unit of work that a user performs (e.g. within a time period), or an action or unit of work performed by a computer or other machine, such as the automatic scanning of a document or the automatic taking of a temperature reading. A "task" may be also the occurrence of an event, such as the arrival of a package, the printing of a document, the end of a time period, etc. In some workflows, tasks may not be expressly mapped (or pre-scripted) by a workflow. For example, as a set of tasks in a workflow proceeds from one workflow participant to another, one task may depend upon, for example, the performance (or the result) of a task performed by a preceding workflow participant (or the result of his or her task).

An electronic workflow may be configured using a set of computer processes implemented on one or more computer processors. An electronic workflow may include a relational database system to track information, e.g. information collected by a WEA. The terms "workflow", "workflow system" and "electronic workflow system" as used herein may also mean an "electronic workflow".

A WEA may allow a user to accomplish a workflow-related task and contemporaneously (or within a time period from performance of the task) interface with an electronic workflow system (e.g. to collect data, to provide a point of security access or to perform a check point function). A WEA may be part of, or may be connected (or connectable) to, an electronic workflow system and may provide a modular, customizable junction where workflow-related tasks may be performed and task-related information can be created or accessed within the electronic workflow. The workflows contemplated may vary and may include:

Enterprise-germane workflows (e.g. track and trace, item/ user authentication, inventory/order control and supply chain data-access workflows);

Consumer-specific workflows (e.g. remote medical/diet/ exercise or other medical or physical monitoring. (Consumer-specific workflows can include consumer-specified, real-time, workflows, that can be custom-created (e.g. on the fly). In such situations, a WEA may, for example, take in data, such as consumer movements or actions, and the processor of the WEA may thereafter automatically translate the data into any required WEA-enabled actions for a workflow); and Reactive workflows (e.g. workflows triggered by a change in data or an event. (For example a change in a workflow may be initiated by detection of counterfeits in a region resulting in the workflow being modified to include an additional requirement for forensic authentication at the point of sale. Other events such as changes in data (product movement) as determined by GPS monitoring could also trigger reactive workflow tasks. More generally, a reactive workflow may be based on real-time analytics of the workflow and the environment in which the workflow acts.)

The WEA, in accordance with an embodiment of the invention permits workflow data to be captured at the item-level. Item-level detail provides data to uniquely identify a specific item (e.g. a specific package of a particular instance of a stock item), and provides detail to distinguish the specific package or item instance from other packages or other instances of the same stock. With item-level detail, for example, the provenance of a specific package of medication may be tracked throughout a system to ensure its safety for a patient. Other uses of item-level detail are also possible and there are many uses of item-level detail. Non-item-level detail is aggregate data, such as 100 shirts of style "xxx" where the data concerning the shirts does not allow one shirt to be distinguished from another.

A WEA may include hardware configurable for task and workflow-access functionality. A WEA may include (and be customized to perform different workflow-related tasks using) one or more workflow-enhancing modules (or WEMs). A WEM may be a plug-in hardware element (that may be interchanged with other WEMs) and may include hardware (e.g. a sensor/transducer, signal converter, signal conditioner, etc.) to provide data to an electronic workflow system through a software service.

A layered software architecture (e.g. as part of the software service) may be provided to facilitate modular use of the WEMs. Such a layered software architecture may allow configurations where multiple WEMs can be added together, "swapped out" (e.g. exchanged), updated, or replaced.

Each WEM (of a modular system) may provide a WEA with specific workflow/task functionality. Any task function that can be tied to a workflow may be enabled by a WEM. For example, a first WEM may provide a 2D barcode reading functionality which may be used for scanning barcode information and tracking a package (at an item-level) through a workflow. A second WEM may allow a WEA to operate as an authentication device for a document (e.g. to validate the genuineness of a deed or other document). A third WEM may allow a WEA to provide user identification (ID) verification functionality.

Additional WEMs may provide customizable functionality (e.g. through a system of interchangeable modules) for other workflows as well. For example, one WEM may provide wireless electrocardiogram (ECG) monitor functionality for monitoring a patents heart and transmitting that information to a workflow. Such a WEM may allow a person to monitor his or her heart function (e.g. at home) and provide that information, for example, to a workflow monitored by a hospital and an insurer. Another WEM may allow GPS position information to be included in a workflow. Such sensing may provide location information for particular items (item-level specific locations) for a track and trace workflow (e.g. for automobile or other valuable item tracking). However, the invention is not limited by the descriptions of WEMs above and many different work task functions (or points of interface between task and workflow) can be provided through a WEM.

The WEMs used by a WEA (and their form) may depend upon the type of function and interface needed in the workflow. As a WEA can be incorporated into many different types of workflows (e.g. enterprise-germane, consumer-specific, reactive), the physical configuration of a WEA may also vary.

For example, a WEA may be a single WEM, or a WEA may be a group of WEMs coupled together. A group of WEMs may be also configured as a custom, stand alone device, such as for a device specific production workflow (e.g. a car assembly production line) or specific medical monitoring (e.g. an in-hospital patient monitoring device).

A WEA, in an embodiment, may include a base device (e.g. a commercially-available processor device) that may be customizable for workflow use through one or more WEMs (e.g. WEMs in the form of hardware plug-ins). The hardware plug-in may include hardware (e.g. sensor/transducer, signal converter, signal conditioner, etc.) to perform a particular task (scanning, authenticating, etc) and to convert sensor data to digitized form (e.g. for transmitting to an electronic workflow system using a software service). For example, a computer device, such as a PC, laptop, notebook, tablet (e.g. including a TouchSmart™ device by Hewlett-Packard Company of Palo Alto Calif. or an iPad™ device by Apple, Inc. of Cupertino, Calif.)-netbook, mini- or personal digital assistant (PDA) may serve as a base device for a WEA, using hardware plug-in WEMs that may be coupled to the base device. Additionally, a consumer mobile communication device such as a cell phone or higher functioning "smartphone" (cell phone with additional computing/connectivity features), such as an iPhone™ device (by Apple, Inc.), Blackberry™ device (by Research In Motion, Inc. of Waterloo, Ontario) or Droid™ device (by Motorola, Inc. of Schaumberg, Ill.) may also serve as a base device for a WEA using hardware plug-in WEMs. Other consumer mobile computer devices, such as an iPod™ device (by Apple, Inc.) or an MP3 player, could also serve as base devices for WEAs, using hardware plug-in WEMs.

Plug-in modules such as a 2D scanner (e.g. for barcode reading), authentication devices, user ID validation devices and even more specialized modules such as one for electrocardiogram (ECG) monitoring can may all be added to a base device to enable workflow-related task and workflow interface functioning. Further, "on-board" functionality (e.g. functionality that is within or integral to the device, such as image or sound capture functionality) of computer devices and mobile communication devices may also be incorporated for workflow use by WEMs that permit communication with an electronic workflow system.

WEMs may include specialized scanning or sensing devices such as scanners, barcode readers and other authentication devices. A WEM, in an embodiment, may include a high-end sensor device, such as for example, a digital microscope, including contact digital microscopes and digital inspection microscopes that provides forensic imaging for discrepancy detection in printed material. The field-of-view of such a microscope may be adapted to be sufficiently wide to be able to capture multiple printed characters/fiducials. Such a device may be configured as a WEM plug-in.

In an embodiment, a system of WEMs for modular, customizable workflow task and interface may be applied to a workflow that incorporates network printing. In such an example, a multifunctional or "all-in-one" printer (a MFP) may be configured with one or more WEMs to make up a task-customizable "workflow kiosk." A workflow kiosk may incorporate printing and other tasks into an electronic workflow using one or more WEMs.

A workflow kiosk may also be made using a device other than a printer, such as a router, PC workstation or other processor device. A MFP with one or more WEMs may be considered a WEA (e.g. a base device (MFP)+WEM(s)). An MFP may be an office machine which incorporates the functionality of a group of previously separate and distinct devices, such as a printer, scanner, photocopier, facsimile machine and email terminal. When configured with additional WEMs, an MFP may perform additional tasks and serve as a point of interface with an electronic workflow.

An MFP, in an embodiment, may be configured with one or more WEMs internally to allow the MFP to provide user authentication and document authentication tasks. Authorization tasks (e.g. allowing a document to be printed or picked up from a printer only with authorization) may be implemented though the use of an internal WEM. In such an example, one or more WEMs may also be connected or "tethered" to a MFP, where the WEMs are external to the MFP.

A WEA (such as a single WEM, multiple WEMs, a base device and WEM(s), or a MFP workflow kiosk device) may serve as a "suite" (or re-usable group) of WEA devices. In such an example, one WEA may perform different tasks (with different WEMs) at different points of a workflow. A WEA, at one point in a workflow, for example, may provide inventory checking or location finding function (using a first WEM), while at another point in the workflow, the same device may provide a security check or authorization point (using a second WEM). A WEA may also serve as an interface point for a number of different electronic workflows using different WEMs.

WEMs may be modularly configurable to themselves or to a base hardware device. For example, WEMs may be added together to themselves or added to or removed from a base device (e.g. a consumer computer device). In such a modular environment, a single device may be used in many different ways in different workflows, individually or in combination with other devices-WEMs may be used in completing specific tasks as required by, for example a processor directing workflow tasks.

Devices contemplated include (but are not limited to) MFPs enabled with tethered/plug in/Bluetooth (open wireless technology standard) modules, generic mobile devices (e.g. computers, PDS, smartphones, cell phones, MP3 players etc.) or custom mobile platforms with expansion slots/Bluetooth modules. Specialized (custom) modules cover workflows in application domains, such as workflows in the investigative, scientific, environmental and healthcare fields (e.g. a mobile ECG application implemented through vibration-sensitive readers on handheld-effective a single lead ECG) etc.

A modular configuration of workflow-enhancing modules (WEMs) for use in workflow-enhancing appliances (WEAs) may provide advantages in use. For example, a modular system of WEMs may allow for optimized WEA device configuration, such as for example, a WEA that may be customized by task with different WEMs. Where a workflow is not fully mapped out and the interaction of an actor/agent (usually human) in the workflow may not be known a priori, a modular configuration of workflow-enhancing modules may allow the actor(s)/agent(s) to perform the different tasks that may be expected of her/them at a task stage depending on the characteristics/state of the workflow.

For example, if a document, which initially was public (or required no security) has become confidential during the workflow, security/forensics may be required that could not have been predicted by the user. In such a situation a WEA such as a workflow kiosk may request a WEA-related action by the agent based on a "real-time" decision of a workflow processor.

A modular system of WEMs may be dynamically configurable, scalable and upgradeable and may allow use of a single appliance (a single WEA) in multiple workflow tasks. Such a modular system may provide an enhancement to the workflow methodology and may provide new opportunities for workflow monitoring and workflow-related services. The modular system may further allow WEMs to be employed in different configurations such as in tethered, and stand alone (handheld/mobile) configurations.

Current device configurations for workflow devices have been formed traditionally as a function of preference, history/current event and compliance/policy needs. The currently-available approaches do not offer a unified solution that addresses the variable touch points in the evolving workflow systems, such as those utilizing item-level data.

Workflow-Enhancing Appliances

Reference is now made to FIG. 1, which illustrates workflow-enhancing appliance (WEA) 10 having a single workflow-enhancing module (WEM) 12, in accordance with an embodiment of the invention.

WEM 12 may gather data concerning item 18 and transmit the data to software service 20. WEM 12 may be interchangeably coupled to a processor (or processor device) operating software service 20. Software service 20, in turn, may forward the data to electronic workflow system 22. In this example, WEA 10 includes a single WEM (WEM 12). However, in other examples WEA 10 may include more than one WEM (a plurality of WEMs) or a base device and one or more WEMs (Base device+WEM(s)). Further examples, such as a WEA that is a custom device (not made from interchangeable modules) are also possible.

WEM 12 may provide a task functionality that can be incorporated into a workflow. Any task that can provide data or can constitute a point of authorization or other checkpoint for a workflow may be represented through WEM functionality.

For enterprise-germane workflows (e.g. track and trace) WEM 12 may be configured for tasks such as validating or authenticating a document (printed matter on a document), validating or authenticating a user, obtaining certification from an inspector's review, determining product or document location, or validating other characteristics of an item.

For consumer-specific workflows (e.g. remote medical monitoring), WEM 12 may be configured to validate the ID of a user and determine his or her location, validate the authenticity of a drug or medication being taken by the user, or obtain certification of a doctor's, nurse's, or medical attendant's actions.

For reactive workflows (e.g. a pharmaceutical distribution), WEM 12 may, for example, be configured to locate and validate at a forensic level, items in the supply chain when counterfeit products are detected. As above, if a document (e.g. a legal document or document concerning a product) has been switched in a workflow to confidential (or needing high scrutiny), then an additional WEM may be required to forensically analyze a given mark in the document, to provide a biometric response, etc.

WEM 12 may include sensor/transducer unit 14—and signal conversion/conditioning unit 16 for enabling task functionality. Sensor/transducer unit 14 may include hardware that measures a physical quantity or aspect concerning item 18. Sensor/transducer unit 14 may measure an aspect concerning item 18 that is relevant to the particular workflow-related task. Sensor/transducer unit 14 may further include hardware that receives and responds to a signal, and may further output a signal, such as a signal representing piezo/displacement, temperature, etc.

WEM 12 may be configured, in an embodiment, to authenticate printed material. In such an example, item 18 may be printed material on a label, document or other item, like a deed, stock certificate, bill of currency or artistic print. WEM 12 may provide functionality to validate or authenticate item 18. In such an example, sensor/transducer unit 14 may include, for example, a 2D scanner (barcode reader capable of reading a barcode or other identifier within the printed material) or sensor/transducer unit 14 may include a high-fidelity imager, such as a wide field-of-view digital microscope, including contact digital microscopes and digital inspection microscopes.

A digital microscope (e.g. that may be incorporated in sensor/transducer unit 14) may include a catadioptric or dioptric, contact-lens based CMOS imaging hardware device capable of high-resolution image scanning at 1:1 magnification and 5 micron (or better) optical resolution, over a field-of-view that is sufficient to enable capture of printed characters and fiducial elements. Such device hardware enables high-resolution scanning and facilitates the capture of both intentional printing shapes and unintentional printing artifacts caused by the printing process and interaction of the ink with the substrate on which printing occurs. Where sensor/transducer unit 14 includes a wide field-of-view digital microscope device, it may be possible to authenticate a document based on the printing of the document itself, rather than requiring the document to include a bar code or other uniquely identifying label.

In another embodiment, the workflow-related task may be to provide user identification. Item 18 in such an example may be a body part of a person, and the workflow-related task may be to provide user identification (e.g. to certify pick-up, delivery, or quality-control inspection of a document or product). For this example, sensor/transducer unit 14 may include hardware for user identification (ID) validation, such as a fingerprint scanner, retinal scanner, voice processing hardware or inertial sensing device (e.g. for gathering handwritten signature biometrics). For user ID validation, an alternative embodiment may provide functionality to inspect a card, badge or other device carried by a user for identification. In such an embodiment, item 18 may be a card, badge or other user-carried device (e.g. a "Smart card" (card with integrated circuits)) and sensor/transducer unit 14 may include a reader, such as a magnetic strip reader or Smart card reader.

Signals from a sensor within sensor/transducer unit 14 may be received by a transducer, which may convert the form of the received signal—e.g. piezo/displacement, temperature, etc., into for example an analog (or alternatively a digital) electrical signal. Signal conversion/conditioning unit 16 may receive the signal output of sensor/transducer unit 14 (for example as an analog signal) and prepare a digital output signal from the received input, such as by performing an analog-to-digital conversion (ADC). Conditioning can be, for example, filtering, which may be analog or digital filtering (done before or after conversion) depending on the application, etc. (e.g. analog conditioning may be done to amplify a signal before the signal conversion. After digital conversion, filtering may be done, for example, to smooth a sampled digitized signal)

Signal conversion/conditioning unit 16 may provide digital output to software service 20. Software service 20 may provide an interface to electronic workflow system 22. Software service 20, for example, may receive data from signal conversion/conditioning unit 16 and may format or otherwise operate on the data, for example, to create usable metadata for electronic workflow system 22. In such an example, the metadata created may be unique to item 18 (e.g. in the form of either document authentication information or user ID information) and hence the data is provided at item-level and specific to the workflow related task. Moreover, this data may be used for downstream authentication—for example in a situation where a reactive workflow requires a capture of forensic information because there has been a change in the workflow—(such as to provide the ability to send a document to a previously disallowed party, etc.) Electronic workflow system 22 may be configured to process metadata received on an item-level as well.

The connection between WEM 12 and software service 20, may be a physical connection, e.g. through a wire (such as through a Universal Serial Bus (USB), FireWire (IEEE 1394 interface), local area network (LAN) or other line-based connection). In an alternative embodiment, the connection between WEM 12 and software service 20 may be through a wireless connection, such as Bluetooth or "Wi-Fi" (Wi-Fi Alliance supported connectivity technology). Any kind of known communication medium may be used. As such, signal conversion/conditioning unit 16 may be configured to output data to software service 20 following the protocol for the communication medium, e.g. 100BaseT (Fast Ethernet standards for twisted cable pairs).

Power for sensor/transducer unit 14 and signal conversion/conditioning unit 16 may be provided by a power source within WEM 12 (not shown). Where the connection between WEM 12 and software service 20 is a connection such as USB or FireWire, power may be supplied by the connection. Sensor/transducer unit 14 may include individual sensor and transducer components or the sensor and transducer components may be combined into units such as a sensor/transducer unit. Signal conversion/conditioning unit 16 may also include separate signal conversion and signal conditioning units. Other configurations of sensor(s), transducer(s), signal converter(s) and signal conditioner(s) in individual and/or combined units are also possible.

Figure 2A:
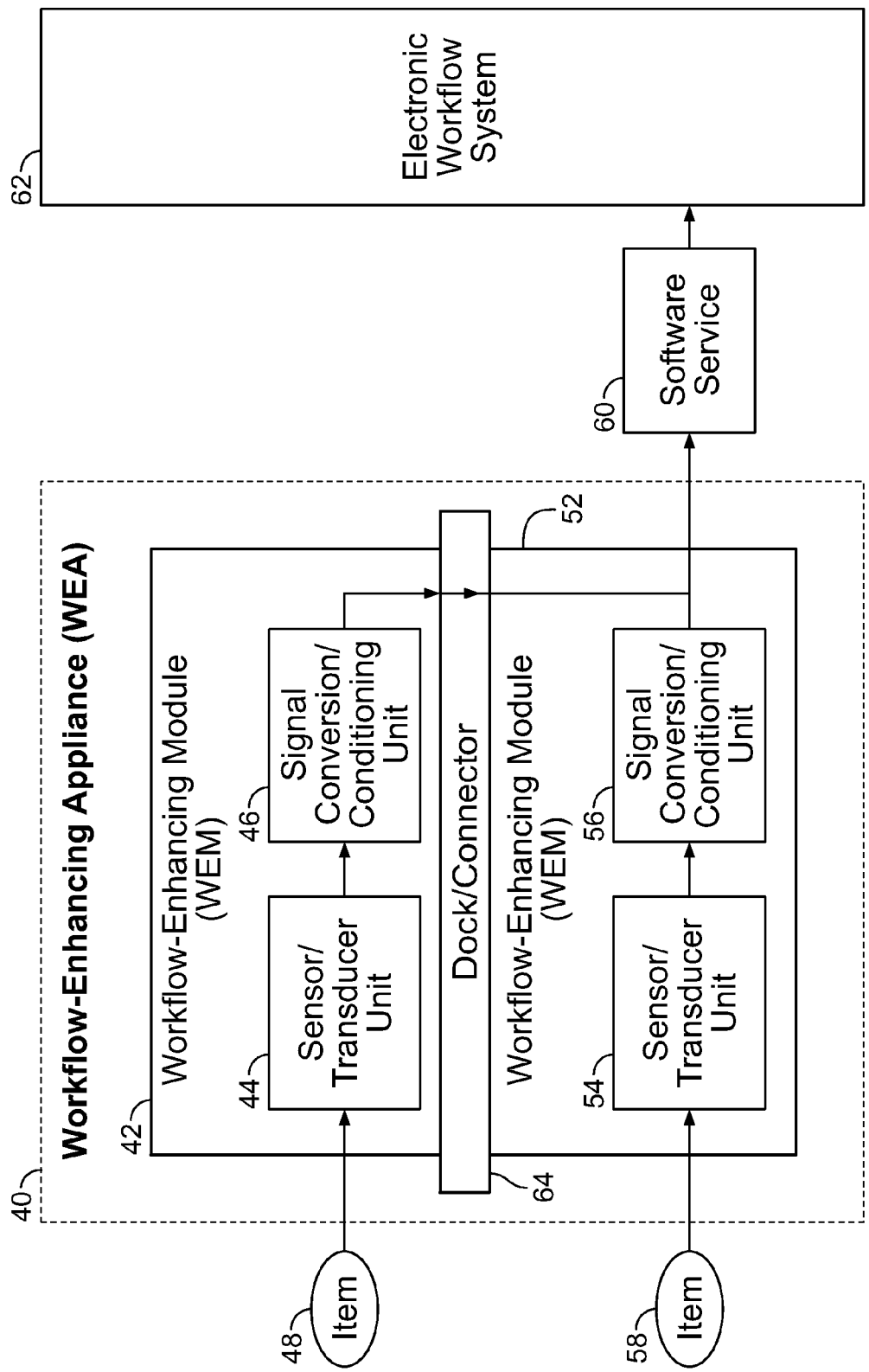
FIG. 2A illustrates a workflow-enhancing appliance in accordance with an embodiment of the invention.

Reference is now made to FIG. 2A, which illustrates a workflow-enhancing appliance (WEA) having multiple workflow-enhancing modules (WEMs), in accordance with an embodiment of the invention.

FIG. 2A depicts a configuration where WEA 40 transmits data to software service 60, and software service 60 (in turn) forwards metadata to electronic workflow system 62. The configuration is similar to the configuration in FIG. 1, however, WEA 40 in FIG. 2A includes two WEMs: WEMs 42 and 52. WEM 42 may include sensor/transducer unit 44 (a unit like sensor/transducer unit 14 above) and signal conversion/conditioning unit 46 (a unit like signal conversion/conditioning unit 16 above). Similar to WEM 42, WEM 52 includes sensor/transducer unit 54 and signal conversion/conditioning unit 56. WEM 42 and 52 may be interchangeably coupled together by dock/connector 64.

WEMs 42 and 52 may provide functionality for different tasks that may be incorporated into a workflow. WEMs 42 and 52 may, for example, provide data or create a point of authorization or other checkpoint for a workflow. Each of WEMs 42 and 52 may provide one of the functions described above for enterprise-germane, consumer-specific or reactive workflows. Dock/connector 64 may be a suitable multi-way connector. For enabling the task functionality, WEM 42 and 52 may include sensor/transducer units 44, 54 and signal conditioner/converter units 46, 56, respectively.

Sensor/transducer unit 44 may measure a physical quantity or aspect concerning item 48 and sensor/transducer unit 54 may measure a physical quantity or aspect concerning item 58. Sensor/transducer units 44, 54 each may convert their respective measurements into signals. Output from sensor/transducer units 44, 54, respectively, may be in the form of analog signals, for example. Signal conversion/conditioning units 46, 56 each may receive analog outputs from sensor/transducer units 44, 54, respectively, and may provide digital output to software service 60. Software service 60 may be operated by a processor (not shown) and WEM 52 may be interchangeably coupled (e.g. through connector 61) to the processor (and thereby may have a link to software service 60).

FIG. 2A shows signal conversion/conditioning unit 56 directly outputting to software service 60, while signal conversion/conditioning unit 46 may output to software service 60 through dock/connector 64. However, the example is not limited in this manner and other configurations are also possible, such as where each of signal conversion/conditioning units 46 and 56 output directly to software service or signal conversion/conditioning unit 56 outputs through dock/connector 64.

In one example, WEM 42 may be configured to authenticate printed material, such as printed material on a label or printed material on a document or other item, like a deed, stock certificate, bill of currency or artistic print. In such an example, item 48 may be printed material, and sensor/transducer unit 44 may include, for example, a 2D scanner or sensor/transducer unit 44 may include a wide field-of-view digital microscope device (described also above), which provides forensic image analysis capability.

In such an example, WEM 52 may validate user identity. Item 58 may be a body part of a person, and sensor/transducer unit 54 may include hardware for providing user identification validation, such as a fingerprint scanner, retinal scanner, voice processing hardware or inertial sensing hardware. (In another example, item 58 may be a card or ID badge carried by a person, and sensor/transducer unit 54 may include a reader, such as a magnetic strip reader or Smart card reader.)

Power for units 44/46 and units 54/56 in WEMs 42, 52, respectively, may be provided by a power source (not shown) within each of WEMs 42 and 52. For example each of WEMs 42 and 52 may have separate power sources maintained separately and not shared between dock/connector 64. Where the connection between WEA 40 (comprising WEMs 42, 52) and software service 60 is a physical connection, such as USB, FireWire or other wire-based connection (where power is supplied), power may be supplied to WEAs 42, 52 by the connection.

Figure 2B:
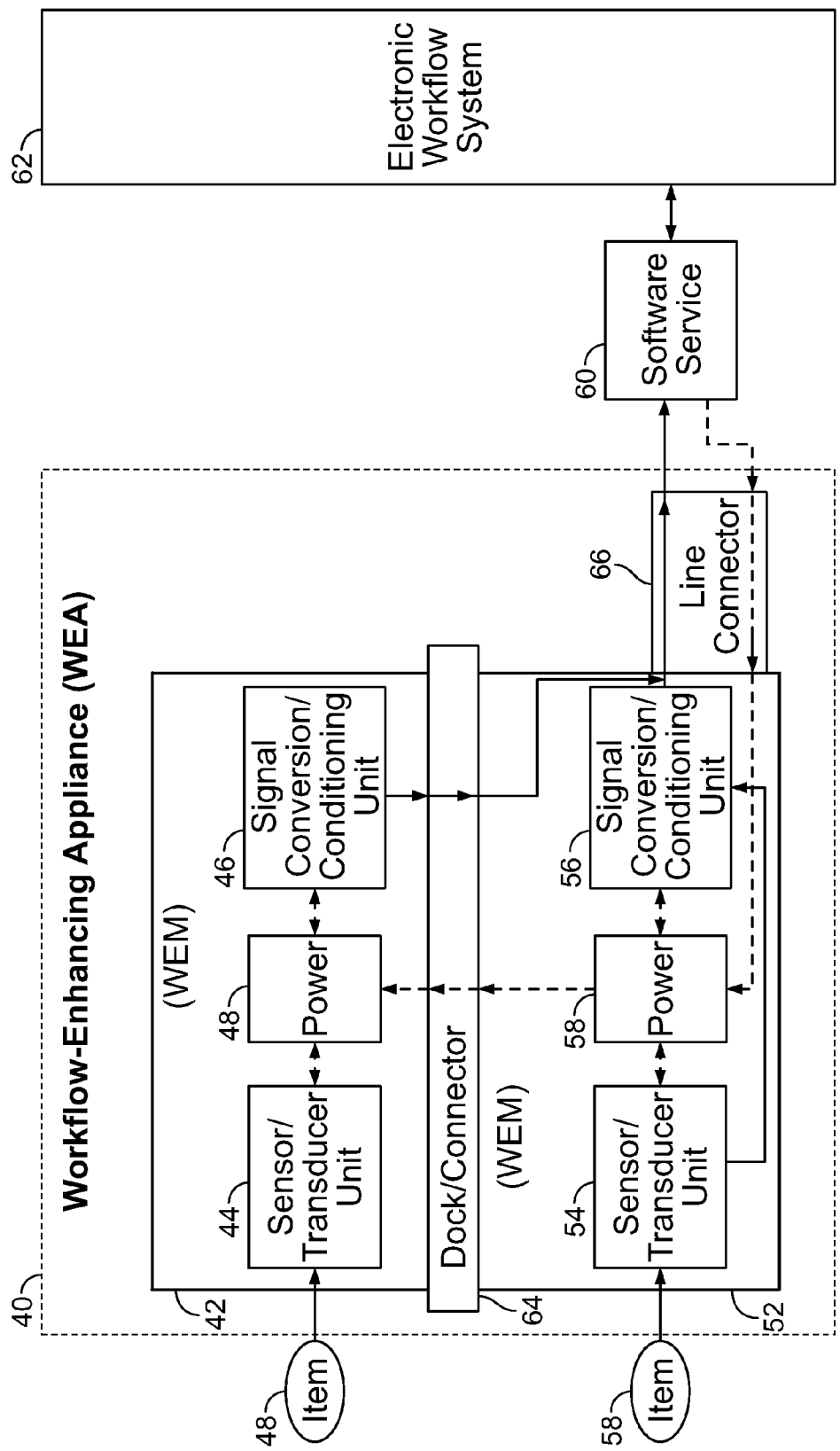
FIG. 2B illustrates multiple workflow-enhancing modules in accordance with an embodiment of the invention.

Reference is now made to FIG. 2B, which illustrates WEMs 42, 52 receiving power through a line connection, in accordance with an embodiment of the invention. FIG. 2B, depicts WEA 40 again with same configuration of WEMs 42, 52 shown in FIG. 2A. Each of WEM 42, 52 (using sensor/transducer units 44, 54 and signal conversion/conditioning units 46, 56 respectively), gathers measurements concerning items 48, 58, respectively, and transmits that information (in digitized form) to software service 60 (which in turn creates metadata and transmits the metadata to electronic workflow system 62).

In FIG. 2B, software service 60 may be a computer system comprising, for example, a processor, computer programming (in a memory) and a power source. WEA 40 may be interchangeably coupled to software service 60 by a line connection, such as a USB, FireWire, Power over Ethernet (PoE) (e.g. IEEE 802.3af-2003 or IEEE 802.3at-2009 standards) or other wire connection that supplies power. In this example, line connector 66, which in this case is part of WEM 52, may provide a location for the line connection to occur between WEA 40 and software service 60. Line connector 66 may be an RJ45 registered jack if it is an Ethernet connection. Alternatively, WEA 40 may be interchangeably coupled to software service 60 by a wireless connection (e.g. Bluetooth or WiFi).

In an embodiment with a line connection, the line connection may include multiple individual lines for power and data transfers. In FIG. 2B a dotted line shows a power line transfer from software service 60 to power connection point 58 in WEM 52. Power may then flow from power connection point 58 to sensor/transducer unit 54 and signal conversion/conditioning unit 56, and, further into WEM 42 through dock/connector 64. In WEM 42 power may flow from power connection point 48 to sensor/transducer unit 44 and signal conversion/conditioning unit 46.

Data may be further arranged to transfer with a corresponding flow. Data from signal conversion/conditioning unit 46, for example, may flow through dock/connector 64 and to software service 60 through the same line that carries data from signal conversion/conditioning unit 56. The line for data transfer for signal conversion/conditioning units 46, 56 passes through line connector 66, which may provide an interchangeable coupling—other WEMs or other WEAs may be connected to software service 60 via the same connection.

Figure 3:
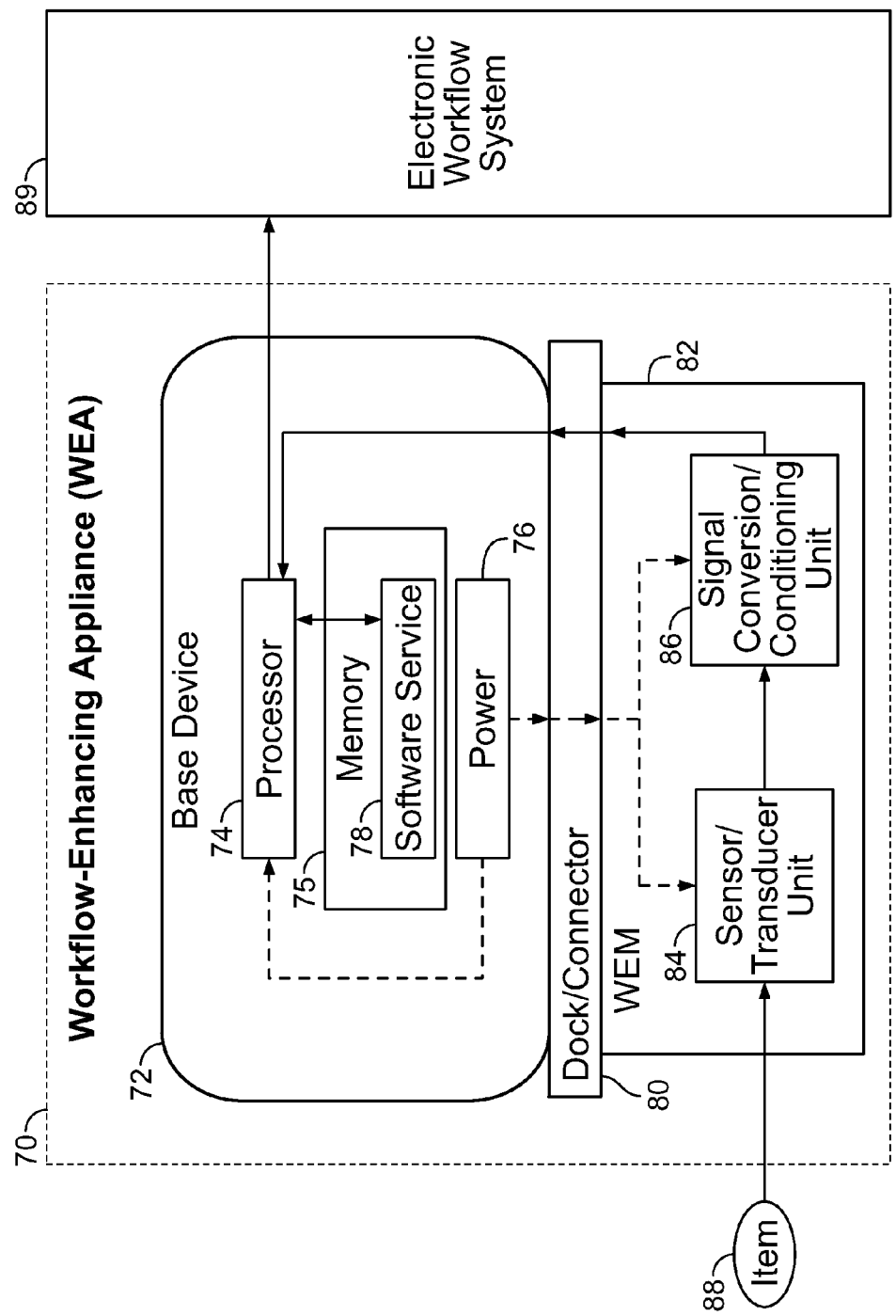
FIG. 3 illustrates a workflow-enhancing appliance in accordance with an embodiment of the invention.

As stated above, a WEA may also be arranged to include a base device (e.g. a device including a processor) and one or more WEMs (base device+WEMs). Reference is now made to FIG. 3, which illustrates workflow-enhancing appliance (WEA) 70, having base device 72 and WEM 82, in accordance with an embodiment of the invention.

In FIG. 3, Base device 72 may be any computer device (a device including a computer processor), such as a PC, laptop, notebook, tablet, netbook or mini-computer, a personal digital assistant (PDA), a cell phone, a smartphone, a MP3 player or other consumer computer device. Base device 72 may include processor 74 coupled to memory 75 and power source 76. WEM 82 may be interchangeably coupled to base device 72 through dock/connector 80. Dock/connector 80 may be Peripheral Component Interconnect (PCI)-based interface or serial equivalent. WEM 82 may be removed from dock/connector 80 and other WEMs may be coupled using the same connection.

WEM 82, like WEMs 12, 42 and 52 (see FIGS. 1, 2A and 2B), may provide a task functionality that can be incorporated into a workflow. In FIG. 3, WEM 82 may be configured to authenticate printed material, such as printed material on a label or printed material on a document or other item, (e.g. deed, stock certificate, bill of currency or an artistic print). In such an example, item 88 may be printed material, and sensor/transducer 84 may include, for example, a 2D scanner or sensor/transducer 84 may include a wide field-of-view digital microscope device (described also above), which provides forensic image analysis capability.

A transducer within sensor/transducer 84 may receive a signal input from the sensor (e.g. the 2D scanner or digital microscope) concerning input read (or measured) by the sensor and may output an electric signal (e.g. either analog or digital). Signal conversion/conditioning unit 86 may receive the electric signal (condition and/or convert the electric signal (e.g. to a digital signal) and provide digital output to processor 74 of base device 72 through dock/connector 80. Processor 74, may process the received digital output using software service 78.

Software service 78, in this example, may be programming that allows processor 74 to interface with electronic workflow system 89. Processor 74 may receives data from signal conversion/conditioning unit 86 and may format or otherwise process the data, using software service 78 programming for example, to create usable metadata for electronic workflow system 89. In such an example the metadata created may be unique item-level data for item 88.

The connection between base device 72 (e.g. processor 74) and electronic workflow system 89, may be a physical connection, e.g. through a wire (such as through a T-carrier (e.g. T1), local area network (LAN) or other line based connection) or the connection between base device 72 (e.g. processor 74) and electronic workflow system 30 may be through a wireless connection (e.g. Wi-Fi). Any kind of known communication medium may be used.

Power for sensor 84, transducer 85 and signal conversion/conditioning unit 86 may be provided by power source 76 within base device 72. Power may flow from power source 78 to sensor 84, transducer 85 and signal conversion/conditioning unit 86 through dock/connector 80.

As described above, a workflow-enhancing appliance (WEA) may be further incorporated into printing environment, for example, to add workflow capabilities and control to printing-related tasks. A multifunction printer (MFP) with one or more WEMs may be operated in an office or other environment as a "workflow kiosk." Routers, PC workstations and other computer devices may also be set up as workflow kiosks in offices and other environments.

Figure 4A:
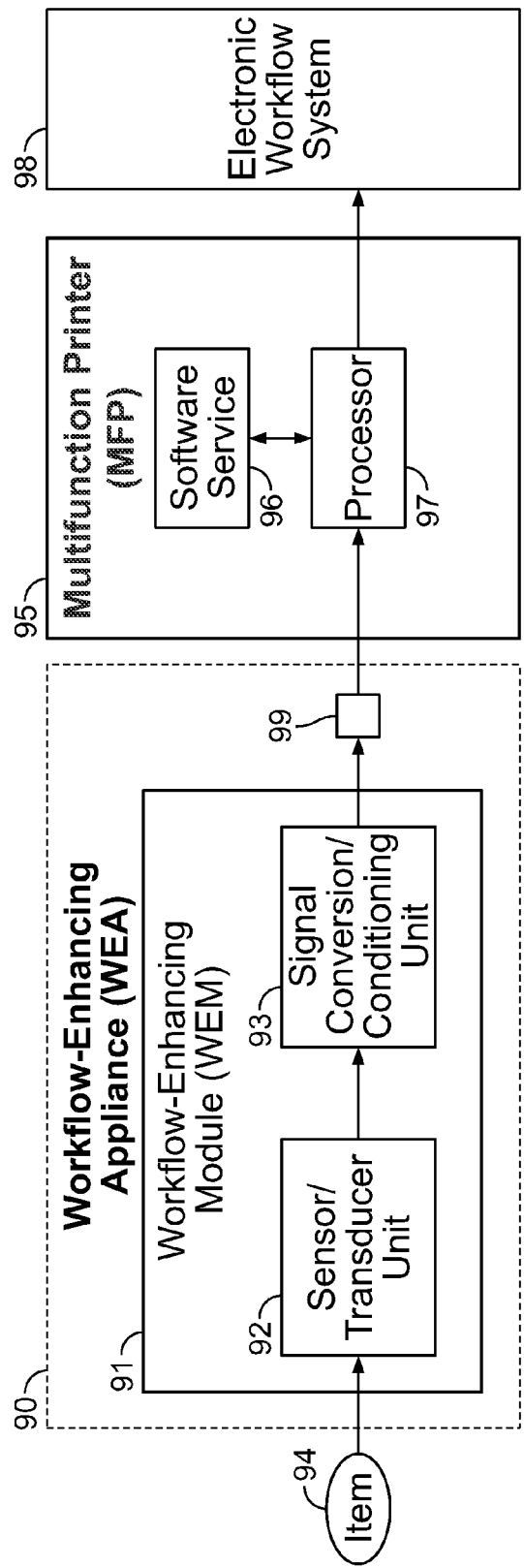
FIG. 4A illustrates a workflow kiosk in accordance with an embodiment of the invention.

Reference is now made to FIG. 4A, which illustrates a workflow kiosk, having a single WEM coupled to a multifunction printer (MFP), in accordance with an embodiment of the invention.

FIG. 4A depicts WEM 91, which may provide a task functionality that can be incorporated into a workflow. In this example, WEA 90 includes only WEM 91. WEM 91 may be configured to authenticate printed material (e.g. deed, stock certificate, bill of currency or an artistic print). In such an example, item 94 may be printed material, and sensor/transducer unit 92 may include, for example, a 2D scanner or a wide field-of-view digital microscope device (which may provide forensic image analysis capability).

In FIG. 4A, WEM 91 may interface with multifunction printer (MFP) 95 to transfer data. Within sensor/transducer unit 92, a transducer may receive a signal from a sensor (e.g. a wide field-of-view digital microscope), and may generate an electric signal (e.g. an analog signal or a digital signal). Sensor/transducer unit 92 may provide that electric signal to signal conversion/conditioning unit 93. Signal conversion/conditioning unit 93 may condition and/or convert the signal and may provide digital output to processor 97 in MFP 95. Processor 97, may process the received digital output using software service 96. WEM 91 may be interchangeably coupled to processor 97, through connection 99 (e.g. which may be part of or external to WEA 90 and may be either a wireless or wire connection). WEM 91 may be exchanged through connection 99 with other modular WEMs.

Software service 96, in this example, may be programming that allows processor 97 to generate metadata from the received signal conversion/conditioning unit output (e.g. from 93) and interface with electronic workflow system 98. Software service 96 may be programming stored in a memory (not shown) of MFP 95. Processor 97 using software service 96, may forward the generated metadata to electronic workflow system 98.

In addition to the above it is also possible that a number of multifunctional printer-type workflow kiosks (or other computer devices connected to WEAs) may be controlled by a centralized-control server in a network.

Figure 4B:
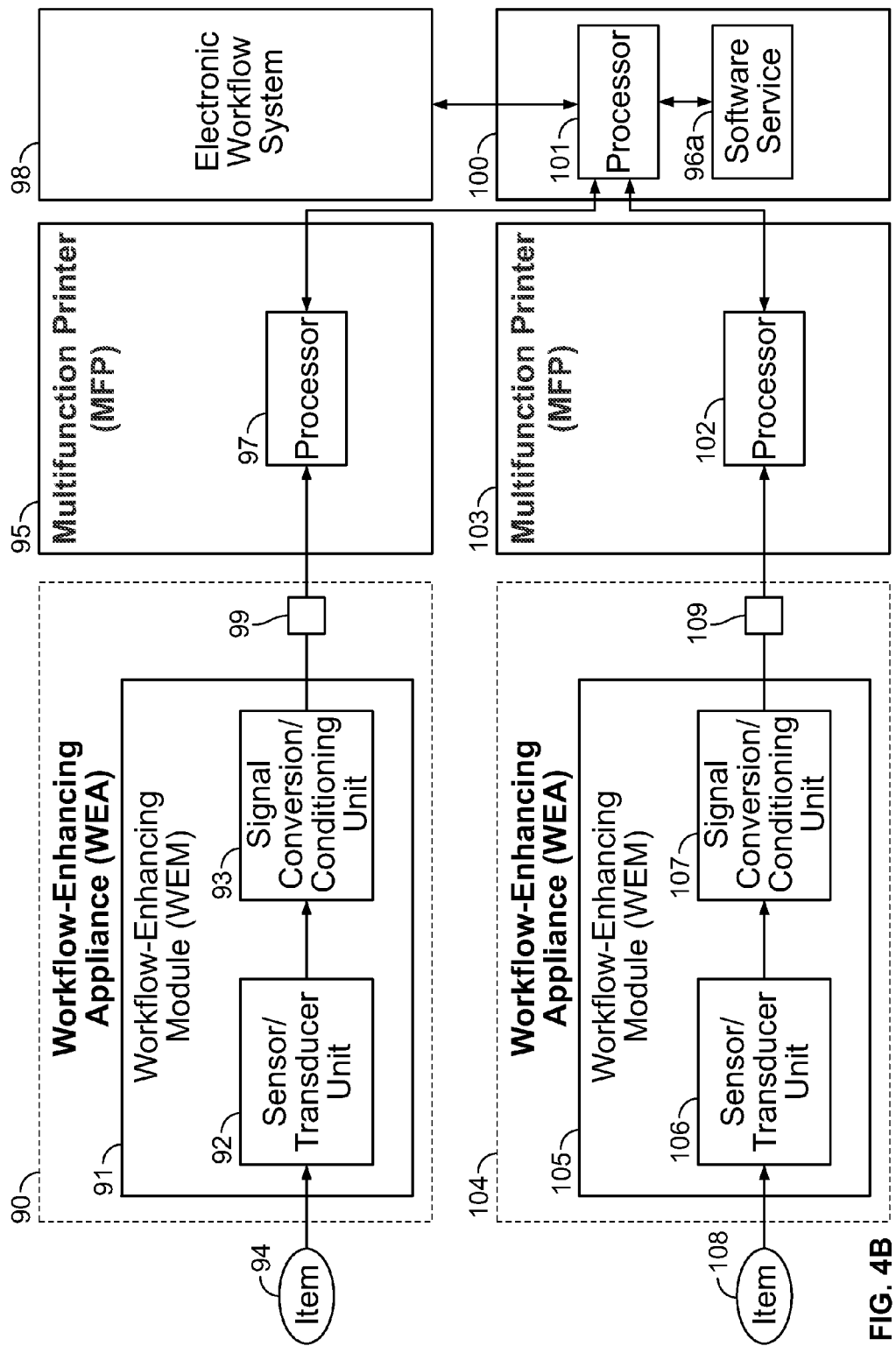
FIG. 4B illustrates workflow kiosks being controlled by a centralized-control server, according to an embodiment of the invention.

Reference is now made to FIG. 4B, which illustrates a network configuration for centralized control of MFPs 95, 103 serving as workflow kiosks. From FIG. 4A, MFP 95 and WEA 90 are depicted. WEA 90 includes WEM 91 having sensor/transducer unit 92 and signal conversion/conditioning unit 93, as in FIG. 4A. Also, WEM 91 is interchangeably coupled to MFP 95 (and processor 97) via connector 99 as in FIG. 4A. WEM 91 gathers information (through sensor/transducer unit 92) concerning item 94 and transmits that information (through signal conversion/conditioning unit 93 to processor 97.

In the configuration of FIG. 4B, however, processor 97 may communicate with, receive instructions from or be controlled by processor 101, which may be located on centralized-control server 100. In such a configuration, processor 101 of centralized-control server 100 may be connected to many different multi-function printers (MFPs) in a network, such as MFP 95 and MFP 103. MFP 103 may include a processor 102 and may be connected to its own WEA 104 (e.g. through connection 109, a wireless or wire connection). WEA 104 may include WEM 105, such as a module for authentication or card reading. WEM 105, like WEM 91, may include a sensor/transducer unit (e.g. 106) and a signal conversion/conditioning unit (e.g. 107). Item 108 may be a label or other document to be authenticated, for example.

Software service 96a (on centralized-control server 100) may provide a service for controlling different WEMs, e.g., 91, 105 that may be coupled to the MFPs in the network. Processor 101, e.g. using software service 96a, may discover devices (e.g. WEMs 91, 105) that have been coupled to the MFPs in the network (e.g. 95, 103). Processor 101 may receive in this example a command from electronic workflow system 98 to perform a task, such as to validate a particular document at a particular MFP (e.g. 103, using WEM 105).

Processor 101, e.g. operating software service 96a, may map (or translate) the received workflow command into a sequence of data collection tasks, where the task may be performed by WEM 105. Processor 101 may load on to processor 102 (at MFP 103) the processing steps for use of WEM 105. Processor 102 may then activate WEM 105 and control the operation of WEM 105 using the control elements downloaded from the centralized-control server 100. Processor 102 may transmit data to processor 101 (at the centralized-control server 100) for re-transmission to electronic workflow system 98 or, alternatively, processor 102 may transmit the data directly to electronic workflow system 98.

Figure 5:
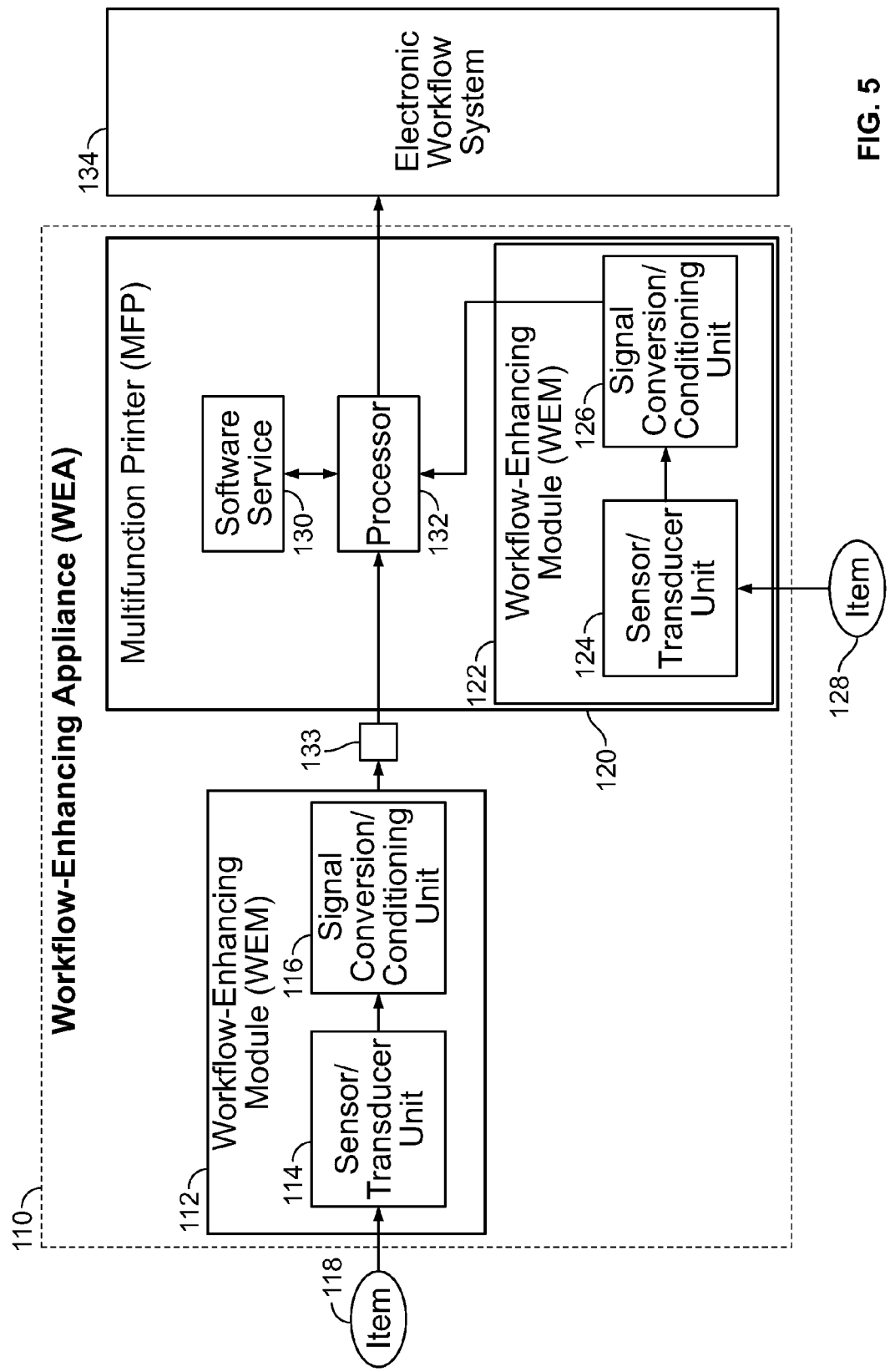
FIG. 5 illustrates a workflow kiosk in accordance with an embodiment of the invention.

Reference is now made to FIG. 5, which illustrates a workflow kiosk, having one WEM incorporated into a MFP and a second WEM interchangeably coupled to the MFP, in accordance with an embodiment of the invention. FIG. 5 depicts WEM 112 interchangeably coupled to MFP 120 (e.g. through connector 133). MFP 120 may further include WEM 122. WEA 110, in this example, includes WEMs 112, 122 and MFP 120 (following the example of a base device (in this case MFP 120) coupled to WEMs (112 and 122)).

WEM 122 may be configured to authenticate printed material (e.g. deed, stock certificate, bill of currency or an artistic print). However, in this example, the authorization capability may be incorporated into MFP 120 through WEM 122. In such an example, item 128 may be printed material that comes to MFP 120 (e.g. though a submitted print job), and sensor/transducer unit 124 (of WEM 122) may include, for example, a 2D scanner or sensor/transducer unit 124 may be a wide field-of-view digital microscope device (described also above), which provides forensic image analysis capability.

WEM 122 may interface with processor 132 of MFP 120 to perform a data transfer. Signal conversion/conditioning unit 126 may receive an electric signal (e.g. an analog signal) from sensor/transducer unit 124 and may provide digital output to processor 132. Processor 132, may process the received digital output using software service 130.

WEM 112 may be interchangeable coupled (or tethered) to MFP 120 (e.g. it is not integral to MFP 120). Alternatively, WEM 112 could be tethered without coupler 133 and the tethering (or a connection to MFP 120 and processor 132) may be achieved by a wire connection or a wireless connection. WEM 112 may provide additional task functionality for workflows. WEM 112 may provide, for example, user identification functionality. Item 118 may be a body part of a person. For this example, sensor/transducer unit 114 may include hardware for providing user identification validation, such as a fingerprint scanner, retinal scanner, voice processing hardware or inertial sensing hardware. (In another example, item 118 may be a card or ID badge carried by a person and sensor/transducer unit 114 may include a reader, such as a magnetic strip reader or Smart card reader.)

Signal conversion/conditioning unit 116 may receive an electric signal (e.g. analog or digital signal) from sensor/transducer unit 114 and may provide digital output to processor 132 in MFP 120. Processor 132, may process the received digital output using software service 130 and output metadata to electronic workflow system 134.

Software service 130 may be programming that allows processor 132 to create metadata from the received signal conversion/conditioning unit output (e.g. outputs from units 116, 126) and transfer the metadata to electronic workflow system 134. In such an example the metadata created may be unique item-level data for items 118, 128, respectively. Processor 132 using software service 130 may process the received signal conversion/conditioning unit data, generate metadata and forward the metadata to electronic workflow system 134.

Figure 6:
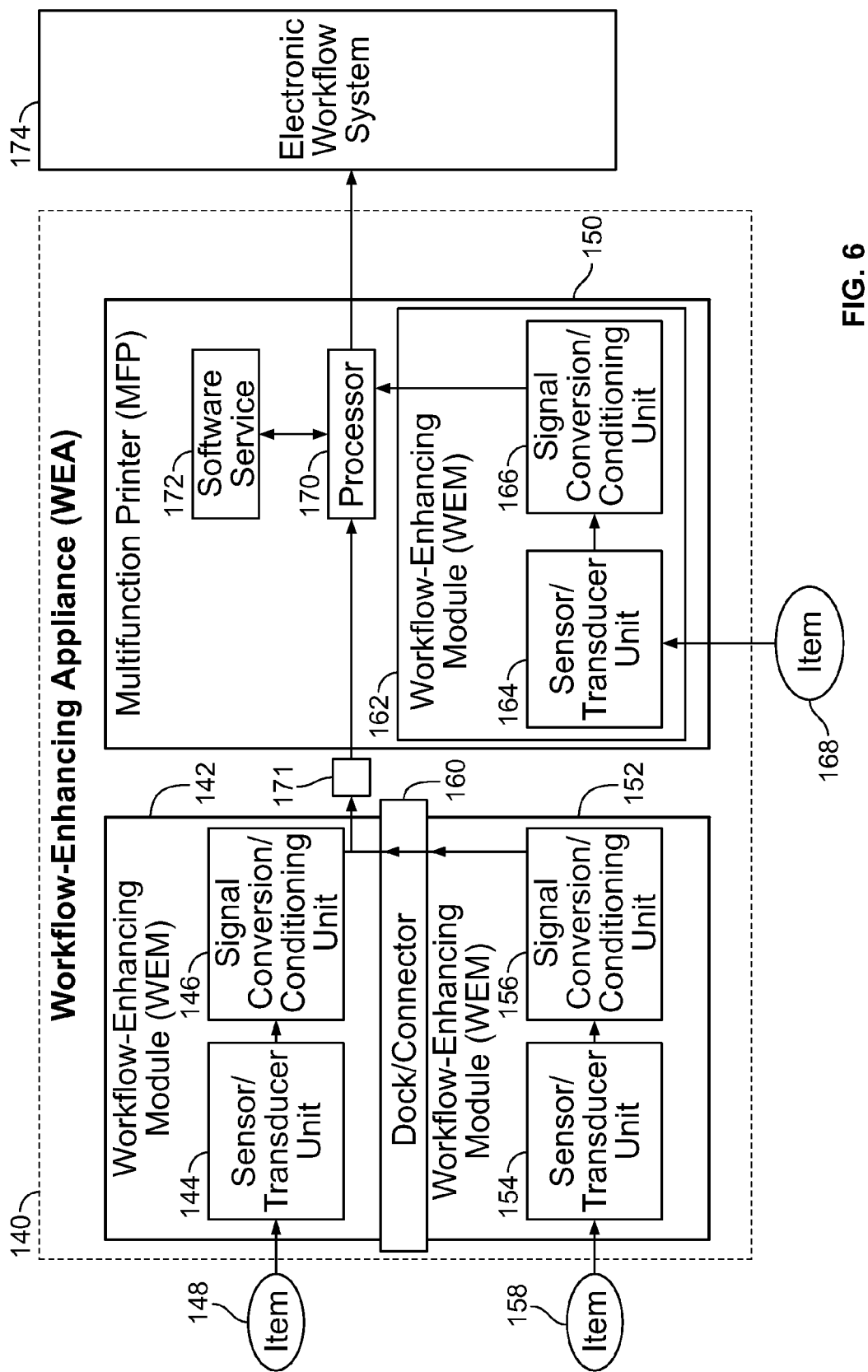
FIG. 6 illustrates a workflow kiosk in accordance with an embodiment of the invention.

Reference is now made to FIG. 6, which illustrates a workflow kiosk, having WEM 162 incorporated into MFP 150 and multiple WEMs (142, 152) coupled to MFP 150, in accordance with an embodiment of the invention. WEA 140 in this example includes WEMs 142, 152, 162 and MFP 150.

WEM 142 may be interchangeably coupled (or tethered) to MFP 150 (e.g. through connection 171, which may be either a physical connector or a wireless connection) and may provide task functionality such as user identification functionality. The coupling may be through a line connection between WEM 142 and MFP 150 or WEM 142 and MFP 150 may communicate through a wireless connection. Item 148, in this example (for user identification functionality), may be a body part of a person.

Sensor/transducer unit 144 may include hardware for providing user identification validation, such as a fingerprint scanner, retinal scanner, voice processing hardware or inertial sensing hardware. (In another example, item 148 may be a card or ID badge carried by a person and sensor/transducer unit 144 may include a magnetic strip or Smart card reader device). Signal conversion/conditioning unit 146 may receive an electric signal from sensor/transducer unit 144 and may provide digital output to processor 170 in MFP 150.

WEM 142 may be further coupled to WEM 152. WEM 152 may further include sensor/transducer unit 154 and signal conversion/conditioning unit 156. WEM 142 may be coupled to WEM 152 by dock/connector 160. Dock/connector 160 may be, for example, a multi-way connector. WEM 152 may provide functionality for a task that can be incorporated into a workflow, such as biometric handwriting analysis (e.g. for validating a signature), fingerprint identification or iris scanning.

Sensor/transducer unit 154 may include hardware that measures physical quantity or aspect of item 158. For example, Sensor/transducer unit 154 may measure the inertial movements of a hand as it makes a signature (or the surface of a finger or an iris). Sensor/transducer unit 154 may convert the measurements into electric signal. Signal conversion/conditioning unit 156 may receive input (e.g. an analog signal) from sensor/transducer unit 154 and may provide digital output to processor 170 for processing using software service 172. In FIG. 6, signal conversion/conditioning unit 156 may output the digital output through dock/connector 160. Data from signal conversion/conditioning unit 156 may flow through dock/connector 160 to the same line (or wireless connection) that carries data to processor 170 from signal conversion/conditioning unit 146.

In MFP 150, WEM 162 may authenticate printed material (e.g. deed, stock certificate, bill of currency or an artistic print). Sensor/transducer unit 164 (of WEM 162) may include, for example, a 2D scanner or sensor/transducer unit 164 may be a wide field-of-view digital microscope device. WEM 162 may interface with processor 170 to perform a data transfer. Signal conversion/conditioning unit 166 may receive analog input from sensor/transducer unit 164 and may provide digital output to processor 170. Processor 170, may process the received digital output using software service 172. Software service 172 may be stored in a memory (not shown) of MFP 150.

Software service 172 may allow processor 170 to create metadata from the received signal conversion/conditioning unit output (e.g. from signal conversion/conditioning units 146, 156, 166) and interface with electronic workflow system 174. In such an example, the metadata created may be unique item-level data for items 148, 158, 168. Processor 170 using software service 172 may forward the generated metadata to electronic workflow system 174.

In the examples provided in FIGS. 1, 2A-B, 3, 4A-B and 5-6, WEMs may be deployed for customized functionality using one or more of the following procedures:

Manual Deoloyment:

(e.g. plug-in of individual WEMs): Manual deployment may be useful for the WEA as a mobile (handheld) appliance, and may further be useful when a WEM is coupled to a base device, like a computer, laptop or smartphone device. A dock for a WEM plug-in may be device docks currently common for peripherals that may attach to devices such as GPS systems, radio-frequency identification (RFID) systems, digital camera systems, etc. Where a WEA is coupled through a dock to a base device, the base device may also provide authorization to activate associated workflow services, either through permissions maintained on the base device or through permissions transmitted from an electronic workflow system.

Docking-Based Deployment:

Dock-based deployment may be useful when one or more of WEMs are incorporated into or make up a tethered appliance attached to another appliance, such as an MFP. WEMs that are tethered, in such an example, can be stored or "docked" in the MFP. As WEMs are docked in the MFP, different modules can be changed out from the tether so WEMs needed for particular workflow tasks can be selected from the dock, with the unnecessary modules being retained in the docking device. The tethered device, in an embodiment, may be pull-out appliance (a base device) from an MFP to which WEMs attach. When the tethered device is not in use, the base device and the WEMs dock in a small place under a control panel, for example, in the MFP.

Functional/Security Applicability-Activated Deployment:

In such a configuration a WEA may be a stand-alone device that incorporates (or may have as plug-ins) many or all of the WEMs for all the workflows it enables, but none of the WEM may work/gather data until an appropriate authorization is provided.

The functionality required for the workflow may dictate the activation or deployment techniques used for the set of appropriate WEMs.

Multiple Appliances/Item-Level Data in Workflows

Figure 7:
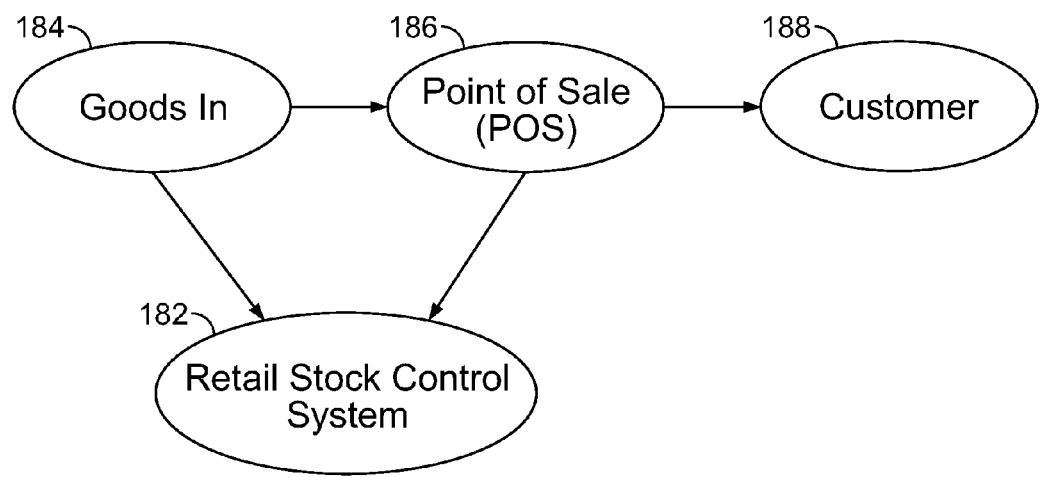
FIG. 7 illustrates a prior art retail workflow system.

Reference is now made to FIG. 7, which illustrates a prior art retail workflow system. In FIG. 7, a retail stock control system 182 collects data for the retailer, for example, in a manner where non-item-level identifiers are used to update inventory stock levels and order data as items pass through a "goods-in" point 184 (e.g. a location where delivery is taken for a quantity of goods) and a point of sale (POS) point 186. Such a system of capturing data using non-item-level identifiers can be related to "just-in-time" (JIT) ordering and, also in relation, to JIT distribution, JIT manufacturing, JIT raw materials ordering and other JIT data collection processes. Therefore, the complete system works on non-item-level data.

In such an example, items may be scanned either at goods-in point 184 or POS point 186 and the inventory for the retailer may be updated. For example, non-item-level stock counts such as 100 shirts (of style "xxx") and 200 pants (of style "yyy") may be listed as the current inventory. Further, non-item-level information may be obtained at POS point 186, when customer 188 makes a purchase. If one shirt is sold, for example, the stock level count for shirts in the retail stock control system goes from 100 to 99. No further information is provided from customer 188 after purchase. All information may be stored in retail control system 158.

Figure 8:
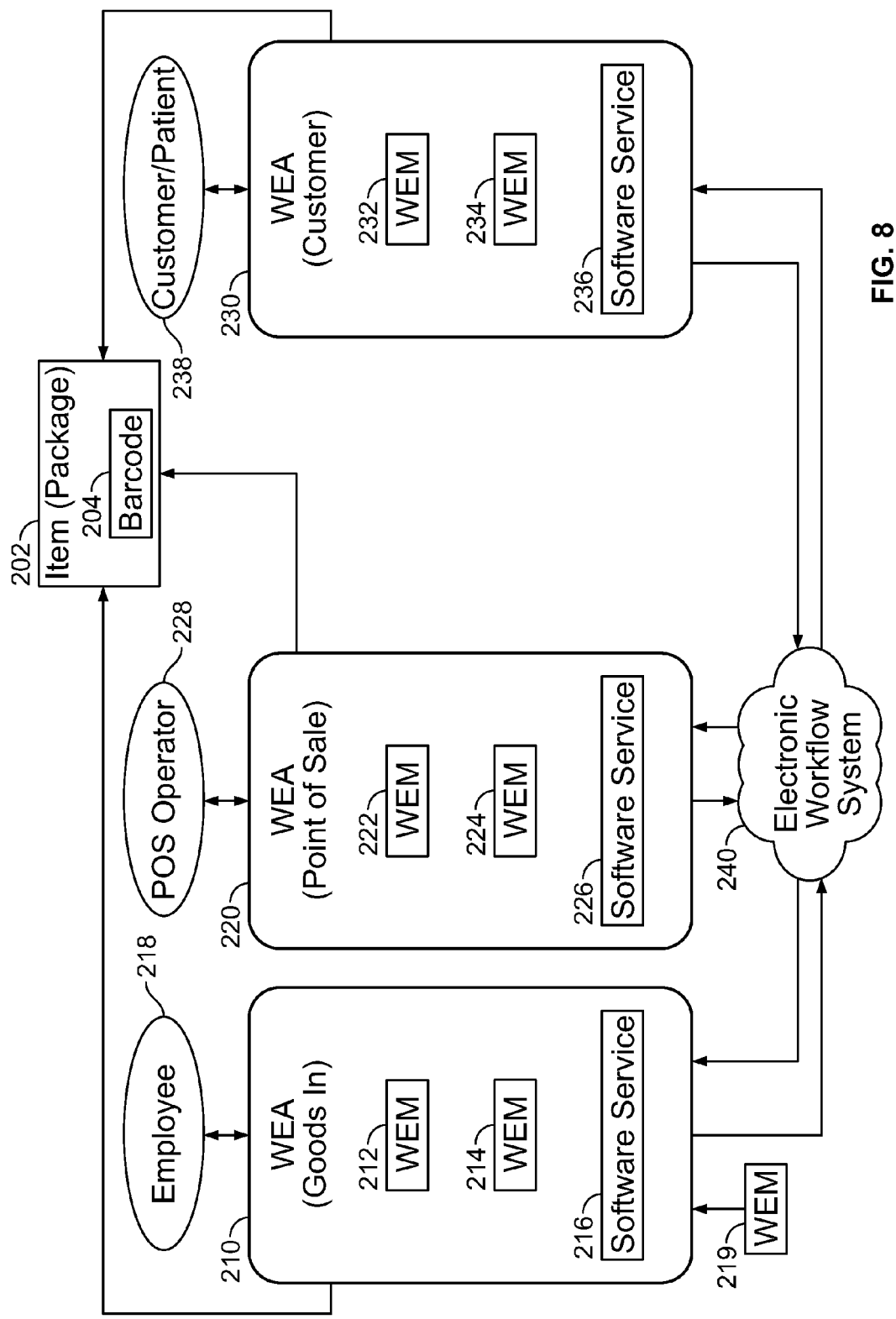
FIG. 8 illustrates a retail workflow system in accordance with an embodiment of the invention.

Reference is now made to FIG. 8, which illustrates a retail workflow system workflow-enhancing appliances (WEAs) capture item-level data and interface with an electronic workflow system, in accordance with an embodiment of the invention. In this example a retailer may be a pharmacy. An item being inventoried, ordered and sold (and hence tracked in a workflow) may be, for example a prescription-only cardiac medication 202.

FIG. 8 depicts WEAs 210, 220, 230, where each may be used for different tasks in the movement of cardiac medication 202. For example, WEA 210 may be used at the point of "goods-in" (e.g. by employee 218), where cardiac medication 202 may be received by the retailer. WEA 210 may include WEMs 212 and 214. WEM 212 may be a 2D barcode reader and WEM 214 may be a GPS sensor. FIG. 8 further depicts WEA 220 being used at a point of sale (POS). WEA 220 may include WEM 222 (e.g. a 2D barcode reader) and WEM 224 (e.g. an authentication device).

WEA 230 may be controlled by customer/patient 238. In FIG. 8, WEA 230 may include WEMs 232 and 234. WEM 232 may be a 2D barcode reader and WEM 234 may be an electrocardiogram (ECG) monitor.

WEAs 210, 220, 230 may be used to perform tasks and interface with electronic workflow system 240. Electronic workflow system 240 may be a computer-based system (in this example computing systems within an Internet computing cloud) for tracking, monitoring or authorizing product movement or product events. Electronic workflow system 240 may include a relational database management system or similar computer system (e.g. within the computing cloud) to store data concerning product movement and events.

Each WEA 210, 220, 230 may communicate with electronic workflow system 240 using software services 216, 226, 236, respectively. WEA 210, 220, 230 may each further include a processor (not shown) to, for example operate software services 216, 226, 236, respectively, and WEMs (212, 214, 222, 224, 232, 234) that may be part of WEA 210, 220, 230, respectively. (Alternatively, software services 216, 226, 236 may be incorporated into electronic workflow system 240, where WEAs 210, 220, 230 include communication facilities).

In the example of FIG. 8, cardiac medication stock (medication, item) 202 may be received at the goods-in location by employee 218. There, WEA 210 may be used to read barcode 204, which may be on the packaging of medication 202. In such an example, employee 218 may use WEM 212 to read barcode 204. A device ID of WEA 210 may be transmitted by software service 216 to access electronic records in electronic workflow system 240. From such access, item 202 (the container of medicine) may be "checked in."

Data for item 202 may be stored in electronic workflow system 240 and GPS data (as well as date and/or time information) may be added to the electronic records maintained for item 202. In registering (or checking in) item 202 (the container of medicine), a small printer/scanner such as an HP sp400™ (wrist-worn all-in-one printer) by Hewlett-Packard Company, for example, may be used as WEA 210 and may incorporate WEM 212 for performing scanning tasks.

Referring again to FIG. 8, customer/patient 238 may require medication and he or she may come to an establishment of the retailer with a prescription. In this example, a person, such as a salesperson or pharmacist (e.g. POS operator 228), may use WEA 220 with WEMs 222 and 224 installed. POS operator 228, for example may scan barcode 204, using WEM 222 (the 2D barcode reader). WEA 220 may then interface with electronic workflow 240 using software service 226. Records in electronic workflow 240 may be accessed to update stock levels and check for circumstances: 1) that may be associated with this kind of cardiac medication in general (e.g. looking at non-item-level data); or 2) that may be associated with package 202 in particular (e.g. looking at item-level data).

In this example, electronic workflow system 240 may transmit to WEA 220 a notification stating, for example, that due to the strong/high-potency nature of the medication, authentication of the medication is required before it is given to customer/patient 238. In such an example, POS operator 228 may use WEM 224 (the authentication device) to verify the authenticity of the medication 202 (e.g. through Raman or other optical imaging techniques capable of performing a "mass spectroscopy" analysis of ingredients). Where a Raman or other such imaging device is incorporated into WEM 224 as the authentication device, WEM 224 may be used to forensically analyze the material of the medicine itself.

Alternatively, WEM 224 may, be a wide field-of-view digital microscope device system, which may be used to forensically identify a mark on the surface of a pill or tablet, or a medical document, label, prescription, etc. This type of authentication using forensic marking would be different than the "mass spectroscopy"-type authentication described in the previous paragraph. WEA 220 (a mobile device) incorporating a wide field-of-view digital microscope also may be used to take a forensic image of a security fiducial (e.g. one or more printed characters/marks (which may be used in a workflow item (e.g. a document) for a particular workflow security need). For example, the security fiducial may be located next to barcode 204. This image derived data may be checked against the original electronic record as well as, for example, chain of custody information or prescription information (such as for verifying the medicine against a "tamper-resistant" (source-verifiable) prescription. If the information matches, customer/patient 238 may receive the medicine.

Following such a sale, customer/patient 238 may take package 202 (the medication) home. Customer/patient 238 may further ingest a dose of the medicine. Because this may be the first time customer/patient 238 has been prescribed this medication, he or she may be required perform a monitoring procedure, such as electrocardiogram (ECG) monitoring, after taking each dose. In such an example, customer/patient 238 may use WEA 230 (which may be a camera enabled smartphone) to capture the 2D barcode (e.g. using WEM 232) and access electronic records from electronic workflow system 240 concerning the medication (e.g. using software service 236). Customer/patient 238 may perform this access using a mobile application, such as one that may be available from organizations such as ScanBuy, Open Mobile Alliance (OMA) or GSI Commerce, or a custom application. In such an example, where access is attempted using a 2D barcode alone, additional authorization may be required to meet negotiated, for example, Health Insurance Portability and Accountability Act (HIPAA) etc. regulations for the application.

In FIG. 8, customer/patient 238 may receive from electronic workflow system 240 an instruction to perform ECG monitoring (using WEM 234) after taking the medication. Customer/patient 238 may administer the ECG (using WEM 234), and data may processed (filtered etc.) either locally (e.g. by software service 236) or by a remote service (e.g. within the Internet computing cloud). The results may be compared to patient's records and limits maintained in electronic workflow system 240. Depending on the result, Customer/patient 238 may be sent either an all clear notification, or, alternatively, a notification not to take any more medication and see consultant.

A further use of a WEA may be seen, when the example of FIG. 8 is modified by a situation where particular counterfeit drugs have been detected within the drug distribution system. In such a situation, there may be a system-wide alert, within electronic workflow system 240 that counterfeit drugs may have been detected. If an alert has been sounded, WEA 210 (e.g. the mobile device at the "goods-in" point of the retailer) may receive a notification (or an alert) from electronic workflow system 240 that additional WEM 219 (a forensic authentication module) is required for "checking in" a certain suspect delivery.

In such a situation, user 218 (the operator at the goods-in location) may then add WEM 219 to WEA 210 (e.g. couple WEM 219 to WEA 210 as a plug-in module) and perform the forensic check, accessing and updating records in electronic workflow system 240 (e.g. using software service 216).

Figure 9:
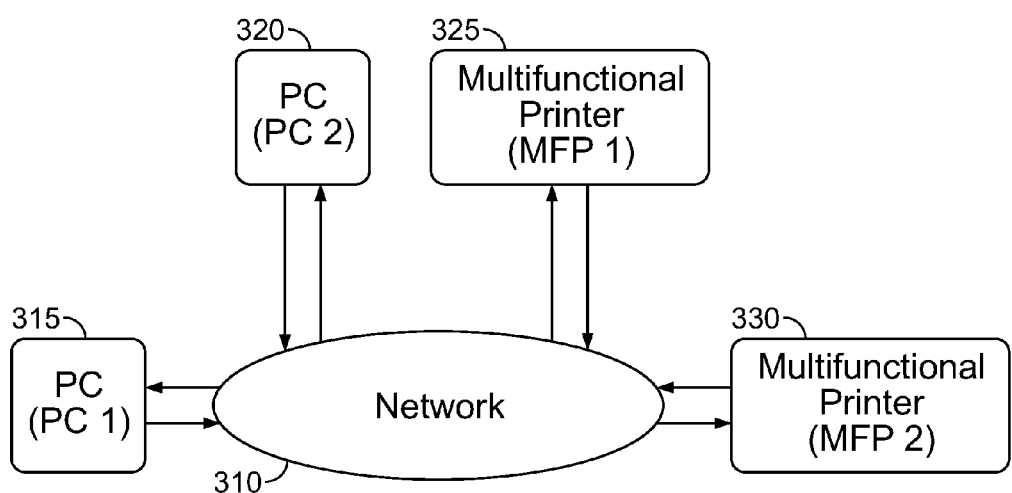
FIG. 9 illustrates a prior art network printing system.

Reference is now made to FIG. 9, which illustrates a prior art network printing system. In FIG. 9, network 310 provides communication links and connections for two personal computers, PC 315 (PC 1) and PC 320 (PC 2). Each of the PCs 315, 320 may access either one of multifunction printers 325, 330 (MFP 1 and MFP 2) using network 310. The PCs 315, 320 may access the printers, but no workflow metadata or workflow interface is created in this prior art example.

Figure 10:
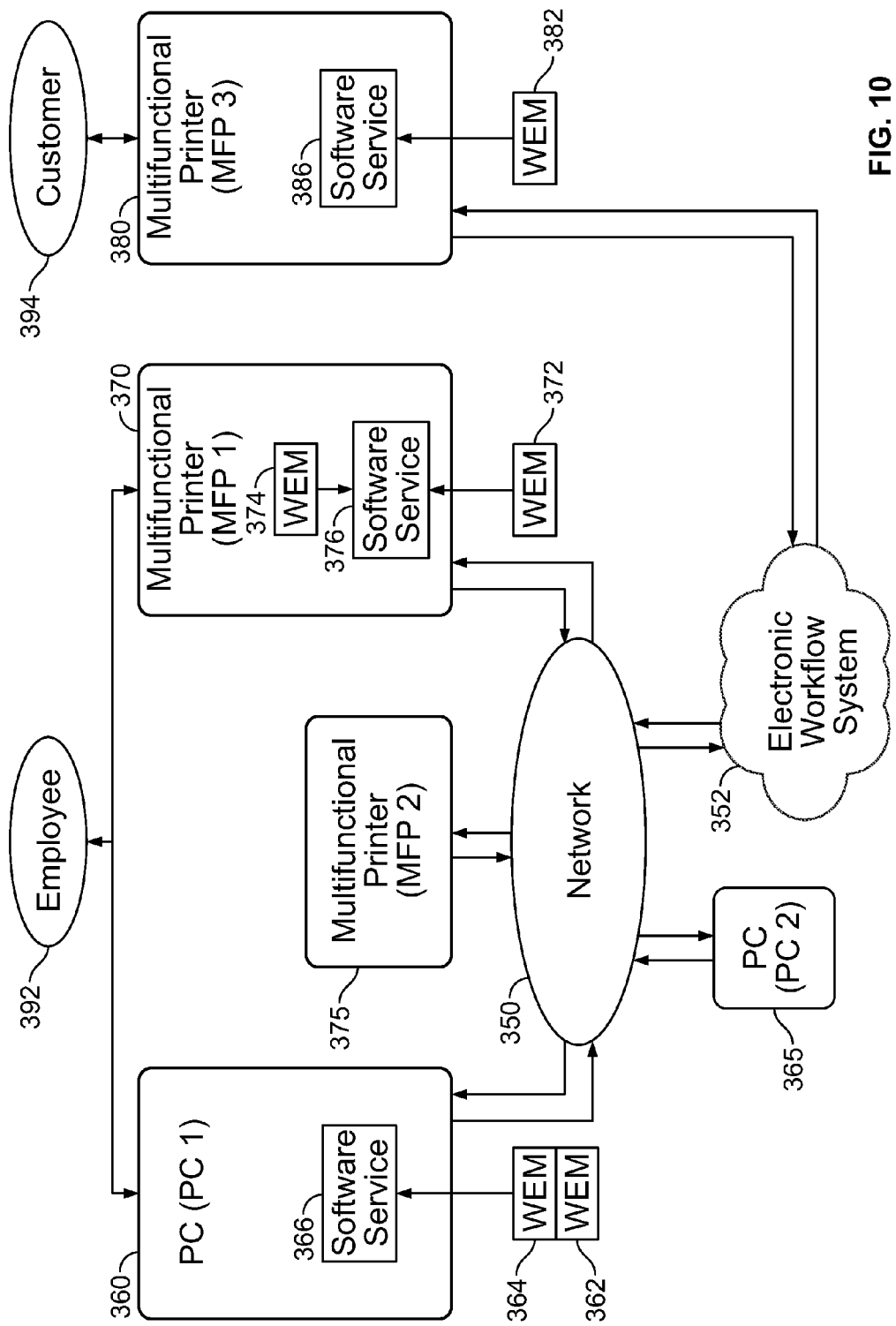
FIG. 10 illustrates a network printing system in accordance with an embodiment of the invention.

Reference is now made to FIG. 10, which illustrates a network printing system using workflow-enhancing appliances, in accordance with an embodiment of the invention. FIG. 10 depicts network 350, with connections to PC 360 (PC 1), PC 365 (PC 2), multifunctional printer (MFP) 370 (MFP 1) and MFP 375 (MFP 2). In this example, network 350 is further connected to electronic workflow system 352. Electronic workflow system 352 may be a computer-based system (such as a group of computing systems including a relational database management system) for tracking, monitoring or authorizing movement or events concerning a document production workflow. Electronic workflow system 352 may include data such as electronic records, document policy information and security information.

PC 360 may be configured with WEMs 362, 364. WEM 362 may be a 2D barcode reader and WEM 364 may be a document authentication device. MFP 370 may be configured with WEMs 372, 374. WEM 372 may be a user identification device and WEM 374 may be a document authentication device. Additionally, MFP 380 is configured with WEM 382. In this example, WEM 382 may be a document authentication device.

FIG. 10 provides an example of a document-based workflow, where MFPs 370, 380 (configured as WEAs and operating as workflow kiosks) and PC 360 (as also configured as a WEA and operating as a workflow kiosk) work together in the handling of a document through a workflow. In this example, a document, such as a legal property deed, may be created and a workflow concerning that document may ensue. Employee 392 may use PC 360 to print one copy of the deed on MFP 370 (MFP 1). MFP 370 may process the printing request, and employee 392 may move to MFP 370 to collect the document. Security may be controlled by electronic workflow system 352. At MFP 370, electronic workflow 352 may enforce a requirement that employee 392 may collect the document only after he or she enters identification. In such an example, WEM 372, a user identification device, may be activated. WEM 372 may be, for example, a fingerprint reader or other user forensic identification device.

Additionally, as the document is being printed by MFP 370 an authentication mark may be scanned during the printing by WEM 374. In such an example, WEM 374 may be an authentication device such as a wide field-of-view digital microscope device for forensic authentication. Such an authentication task may be required from previous state in the workflow, or the need for an authorization may have resulted from an event in the current state of the workflow. The use of a forensic mark, or the need for one (and the specification of what to use as one) may be defined on the fly, just as the document is being printed, for example, because of a change in the overall workflow; i.e. a reactive change.

In this process, unique data may be collected and registered to the document ID through a transmission to electronic workflow system 352. The transmission may occur via network 350 using, for example, software service 376.

In FIG. 10, employee 392, after collecting the document may proofread it and then may register the proofreading action by scanning the authentication mark on the document using WEM 364 at PC 360 (PC 1). PC 360 may have been configured with WEM 364 (an authorization device), which may be used at PC 360 to register the action. Data may be collected by WEM 364 and then transferred using software service 366 to electronic workflow system 352 (via network 350). Employee 392 may then send the document to customer 394.

Customer 394 may validate the document using MFP 380 (MFP 3) configured with a WEM (e.g. 382) that is an authorization module. (Another WEA, such as a PC coupled to a WEM that is an authorization module may also be used.) The authentication process of WEM 382, in this example, may send details of the content of the document to electronic workflow system 352 (e.g. using software service 386) and software service 386 may compare the gathered information against data saved in 352 to as a check against document tampering or other forms of fraud, such as copying, high-res replication, substitution, etc.

Layered Software Platform

An embodiment of the invention may further provide a layered software platform (infrastructure) for operation of a WEM. For example, a layered software platform may be provided in WEAs such as a multifunction printer or computer workstation configured as a WEA or a, PDA, cell phone, smartphone, barcode reader or other computer device configured as a WEA. A WEM that is a stand-alone device may also include a layered software platform for operation. Further, a layered architecture may be used in a network configuration, where, for example, many workflow kiosks are controlled or interface with a centralized control server (e.g. by a managed service).

For a WEA such as a multifunction printer (or for a server controlling a number of workflow kiosks), a layered architecture may be provided through an extension to a platform such as the "Open Extensibility Platform" (OXP) of the Hewlett-Packard Company of Palo Alto, Calif. The OXP platform may include three main layers covering, for example: 1) device, 2) management and 3) workflow.

Figure 11:
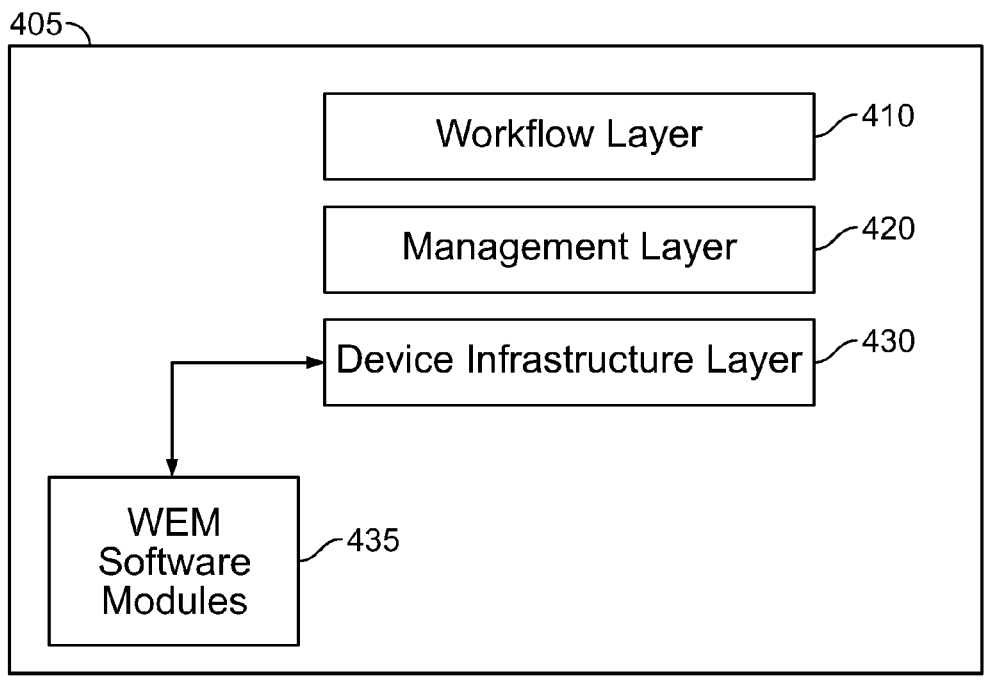
FIG. 11 illustrates a layered software platform in accordance with an embodiment of the invention.

Reference is now made to FIG. 11, which illustrates software platform layers which may be suitable for operation of WEMs through devices such as a multifunction printer. FIG. 11 shows layered architecture 405, including workflow layer 410, management layer 420 and device infrastructure layer 430.

Workflow layer 410 may provide job submission, routing, tracking, data archive and document transformation services. Such a layer may operate by defining a job and a document. Workflow layer 410 may translate extant and nascent workflow requirements into tasks that require hardware associated with a kiosk/base device. For example, when a device (WEM) is added to a kiosk, the device's capabilities are automatically added by matching the device specs to defined WEM software module(s) 435 that are, for example, located in device infrastructure layer 430. Device infrastructure layer 430 may provide marking, digital sending, copying, document finishing and I/O services. Device infrastructure layer 430 may interact with the user, for example, in converting documents to and from paper. Management layer 420 may provide fleet and solution management and configuration services (e.g. services to manage multiple printers or workstations). Management layer 420, for example, may discover devices, track pages processed and kiosk usage.

Within a managed service using a network configuration (where the layered architecture is operated from a centralized control server, see e.g. FIG. 4B), only certain devices (e.g. certain printers in a network) may have certain WEM software module(s) 435 enabled through the presence of WEAs. In implementation, such a configuration may be conceptually no different from searching on a network for a machine (printer) that has stapling, 2-sided printing, legal-sized paper, etc. The set of kiosks or MFP/all-in-one/printing etc devices in a network may be managed together through management layer 420, as part of a managed service.

WEM software module(s) 435 in a network configuration using a centralized control server may be centrally maintained, and not separately stored on each kiosk device. In such an example, each kiosk in a network may search for all of the WEM software modules 435 corresponding to all the WEMs that can be accommodated by WEAs on the particular kiosk, and so (dynamically) each kiosk, in a centrally managed system may offer the latest, fullest set of WEAs possible. (However, in a different example, each kiosk can host the WEM software modules, and in such a system may require further upkeep of the software). WEM functionality may be written akin to how applications (or "apps" for devices, such as mobile devices (e.g. iPhone™), WebOS, etc. are written, for example, taking into account the sensors that are available, writing new apps involving at least one of the available sensors.

One use for a device (such as a MFP) operating with a layered architecture (e.g. through a centrally-maintained WEM-software service) may be to associate metadata with a scanned document being sent to a workflow. Using a layered architecture, such as that depicted in FIG. 11 (e.g. an extension of an operating system such as the OXP™ system), an application may discover the devices to be configured (e.g. the WEMs that are coupled to the MFP or other base device) and then configure the devices to associate, for example, a button on the front of the device with a Web-services call.

Figure 12:
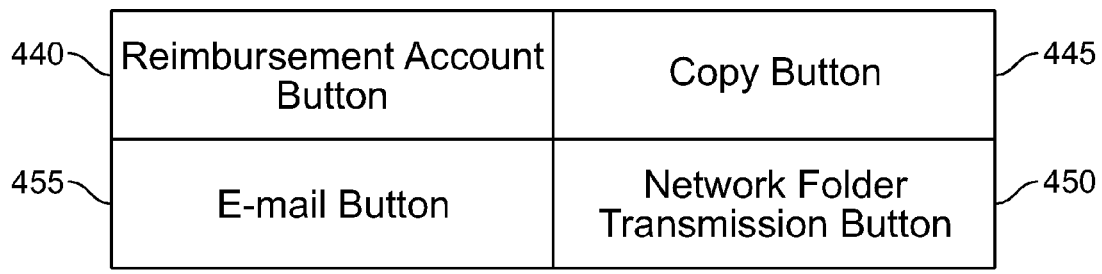
FIG. 12 illustrates a button-based interface in accordance with an embodiment of the invention.

Reference is now made to FIG. 12, which illustrates a set of buttons which may be included in a device such as a MFP. FIG. 12 depicts reimbursement account button 440, copy button 445, network folder transmission button 450 and e-mail button 445.

In such an example, when a user touches a button, such as for example reimbursement account button 440, a dialog box may appear (e.g. when enabled for a Web-services call) to retrieve an account number, such as a number for a bank account, a retirement/401(k) account, a credit balance, an order account, an active case account, a customer list, etc.

After the user enters the account number, a procedure such as a "scan-to-PDF" procedure may occur (e.g. where a document is scanned and a Portable Document Format (PDF) file is created) and a transfer may occur where the generated PDF file is transferred to a specified location (for example to a location in an electronic workflow system).

Many different information transfers and authorizations may occur using a device such as a multifunction printer (MFP) configured using a layered architecture that incorporates a modular WEM system. With such a system of dynamically changeable WEMs developers may produce a wide variety of applications pertaining to workflow use. Because, in general, a WEA may be used to add information to the workflow, many different information transfers may occur for example using a MFP configured with a flexible, layered architecture. Example applications include forensic/security, biometric, environmental (GPS, temp, humidity) and informational (e.g. WiFi-ing more data, synching calendar, product status, etc., data to a printout location-incorporating into a barcode, etc.) types.

Figure 13:
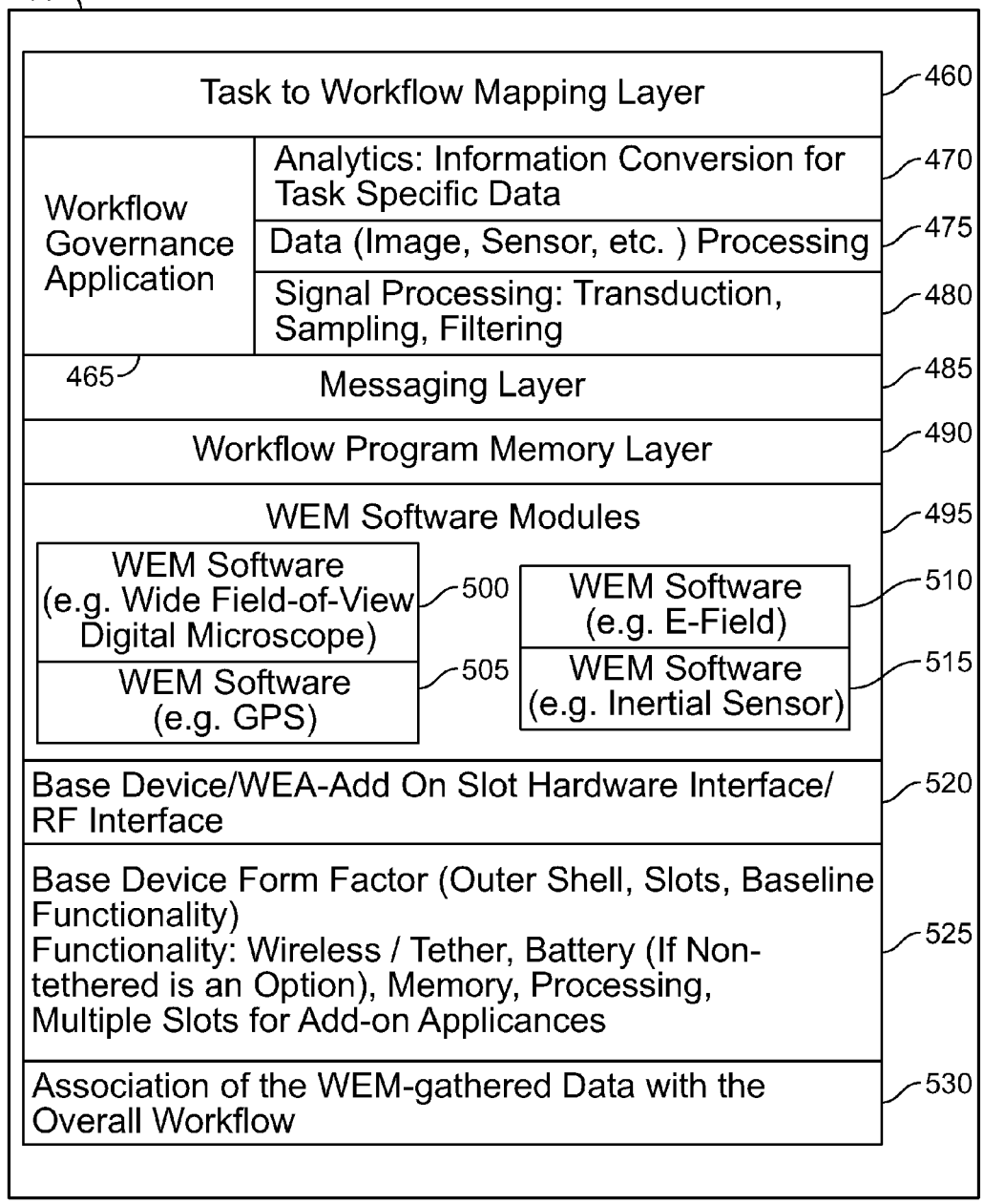
FIG. 13 illustrates a layered software platform in accordance with an embodiment of the invention.

Additionally, a layered software platform may allow for the operation of WEMs in configurations, where, for example, a WEM may be coupled to a mobile base device, a computer workstation (e.g. other than an MFP using an OXP operating system) or where a WEM is incorporated into a stand alone device. Reference is now made to FIG. 13, which is an illustration showing layered architecture 456 for a processor of a base device (such as a computer, PDA, cell phone, smartphone, barcode reader) or a stand-alone device of a WEA.

In FIG. 13, task to workflow mapping layer 460 may be a top (highest or most abstract) layer. Task to workflow mapping layer 460 may translate workflow commands (e.g. commands received by an electronic workflow system for a task) into a set and sequence of WEM-related commands needed for the task. In such an example, task to workflow mapping layer 460 may take a set of instructions for a task and map them to a sequence of WEM operations needed to accomplish them.

Workflow governance layer 465 may translate the sequence of WEM operations into a corresponding set of data collection tasks. Such data collection tasks may include data transduction, sampling, filtering, processing and analytics. Sub-layer 470 may provide analytic processing for task specific data and information conversion. Sub-layer 475 may provide data processing for image and sensor data. Sub-layer 480 may provide processing for signals, such as transduction, sampling and filtering of signals.

Messaging layer 485 may provide programming to load the processing task execution instructions (such as instructions for the data collection tasks) onto the processor controlling the sensor, transducer, and signal conversion/signal conditioning unit of the WEM. Because WEMs may provide services, the WEM software module(s) may map specific workflow tasks to hardware tasks that need occur. As shown in FIG. 13, the WEM software module(s) 495 include but are not limited to the software to capture input from the wide field-of-view digital microscope, etc. devices.

FIG. 13 shows workflow program memory layer 490 and a layer also of WEM software module(s) 495. WEM control modules (in layer 495) may provide instructions to drive the WEM devices. FIG. 13 shows WEM software 500 (to control a wide field-of-view digital microscope device), WEM software 505 (to control a GPS device), WEM software 510 (to control an E-field device, which may be used to gather biometric data such as ECG signals) and WEM software 515 (to control an inertial sensor, e.g. for gathering biometric information). Other WEM software module(s) 495 for other workflow functions are also possible.

If applicable, one or more base device layers (e.g. layers 520 and 525) may be further provided in the layered architecture. For example, FIG. 13 shows layer 520 for base device or WEA add-on slot hardware interfaces. Layer 520 may also provide a radio (RF) interface for wireless communications. Layer 525 may provide programming for base device functionality (e.g. outer shell, slots, and baseline functionality), power and other functionality for wireless or tethered applications (e.g. using a battery if non-tethered is an option), memory use functionality and processing functionality (e.g. including programming for additional WEA add-on slots).

Applicability of base device layers 520 and 525 may be determined on factors, such as ergonomics (ease of use), security, reliability, cost, exchangeability, sustainability/power usage, etc. A further layer for associating of WEM-gathered data with the overall workflow (e.g. an electronic workflow system) is provided at layer 530.

For portable WEAs, the optimal device configuration may be a function of, for example, user preference, history, compliance and/or policy needs. A single portable WEA may be crafted for a particular task—such as track and trace-based on a layered architecture, and that device may be configured with WEMs to perform different tasks which may be included in a workflow. Examples of simple retail tasks in the workflow include:

Track and trace (product tracking);
Interrogate (e.g. barcode scan) a product with a device an get a coupon;
Download product information (such as ingredients or parts);
Download product provenance (e.g. to determine if the product would cause an allergic reaction peanut allergy);
Point of Sale (tracking product sales on an item-level);
Inspection (assessing damage to products on an item-level);
Authentication/counterfeit detection;

Target users, in this example, run the gamut from consumer, retailer, distributor, inspector, manufacturer to forensic agents. The same WEA can be customized for use by different actors at each node (or point) in the supply chain/workflow.

Process Flows

Figure 14:
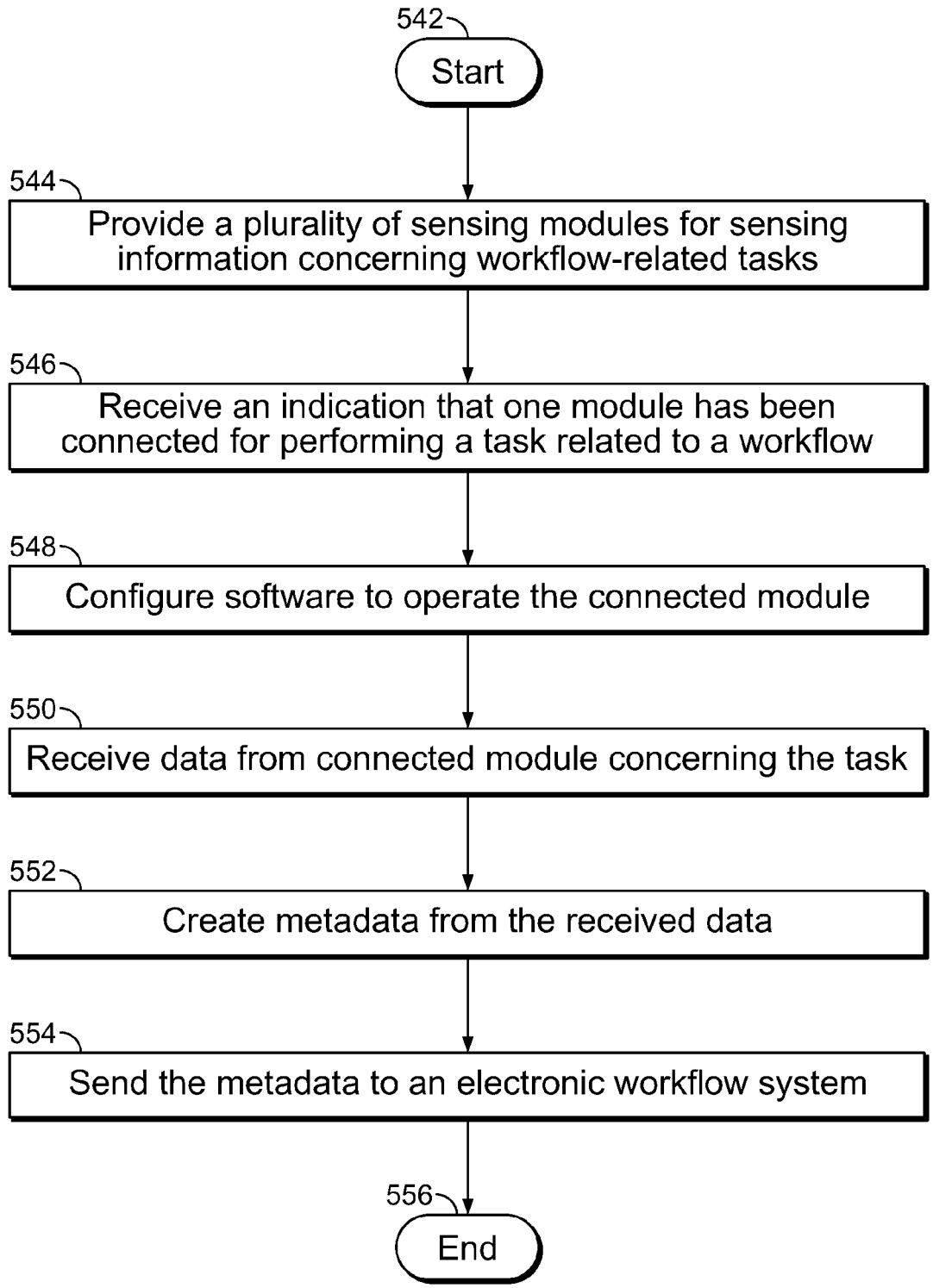
FIG. 14 illustrates a process in accordance with an embodiment of the invention.

Reference is now made to FIG. 14, which is an exemplary process flow diagram for gathering data in an electronic workflow system using a system of sensing modules such as WEMs.

The process may being at step 542, and in step 544 the system may provide a plurality of sensing modules (such as WEMs) for sensing information concerning work-flow related tasks (e.g. tasks monitored and/or controlled by an electronic workflow system). In step 546 a processor, such as one operating a software service, may receive an indication that one module from plurality of modules has been connected to a processor device (e.g. a multifunction printer, base device or other processor device) for performing a task-related to the workflow. For example a WEM for performing 2D barcode scanning or a WEM for performing document authorization using a wide field-of-view digital microscope device may be connected.

In step 548 the processor, such as the processor operating a software service, may configure software within the software service to operate the selected module (the selected WEM) by loading control software that corresponds to the one module being connected. As shown in FIG. 13, layered software architecture 456 may contain a layer (e.g. layer 495), for loading modules such as WEM software 500 for operating devices such as a wide field-of-view digital microscope. Such control software may be loaded upon receipt of a connection command.

In step 550, the processor may receive data from the one module (the connected WEM) that is performing the task related to the workflow. In such an embodiment, a WEM such as a wide field-of-view digital microscope authorization service may transmit data concerning an authorization process performed on a document. In step 552 the processor, e.g. using routines from of the software service, may create metadata records from the received data that are usable in an electronic workflow system. In step 554, the processor sends the metadata to the electronic workflow system and in step 556 the process terminates.

Figure 15:
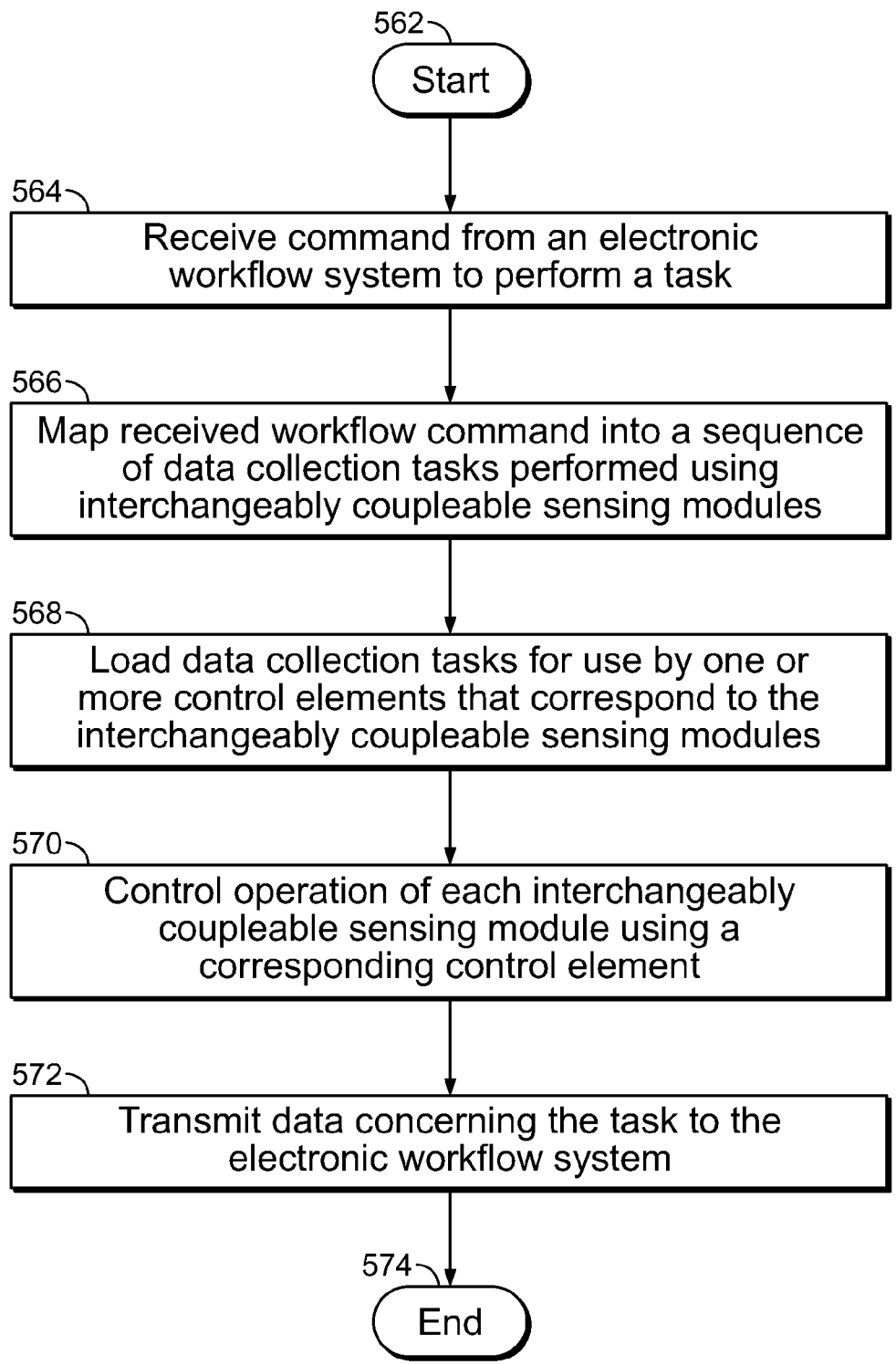
FIG. 15 illustrates a process in accordance with an embodiment of the invention.

Reference is now made to FIG. 15, which is an exemplary process flow for operating a workflow where an electronic workflow system controls the operation of a WEM.

In FIG. 15, the process begins in step 562, and in step 564 a processor, such as one operating a centralized control service for a network of workflow kiosks, may receive a command from an electronic workflow to perform a task. The task may be, for example, to validate a document, to check the provenance of a package, or restrict the access of a document to only users who are authorized to see a document with proper security clearance.

In step 566, a processor, e.g. operating a centralized-network service, may map (or translate) the received workflow command into a sequence of data collection tasks, where the tasks may be performed, for example, by one or more interchangeably coupleable sensing modules. Such interchangeably coupleable sensing modules may be the WEMs described above, for example with regard to FIGS. 1, 2A-B, 3, 4A-B and 5-6.

In step 568, the processor may load on to a WEM processor (e.g. to the processor of the workflow kiosk) processing steps for use by one or more control elements (e.g. WEM software 500, 505, 510, 515 of FIG. 13), where the one or more control elements correspond to the one or more interchangeably coupleable modules at the kiosk.

In step 570, the processor at the kiosk activates the selected modules (the one, selected WEM) and controls the operation of the one module using the corresponding control element. In controlling the operation of the one module, the processor at the kiosk may receive data and create, for example, metadata concerning the operation of the module. In step 572, the processor may transmit data concerning the task (e.g. in the form of metadata created from the data received from the module) to the electronic workflow system. In step 574 the process terminates.

An embodiment of the invention may provide a scalable system that addresses the variable situation dependent requirements of interaction with item-level workflows. A WEA may provide an optimized device configuration based on a workflow need.

As more systems may be developed to tie physical items to electronic records, modular devices that may be focused on diverse physical/electronic world interaction (rather than the current single function model of workflow device) may be useful for workflow tasks. Such devices may increasingly be of value to anyone wishing to customize their electronic/physical world interfaces. Such customization may be based on different preferences for privacy, security, connectedness, medical needs, location, etc.

Additional Considerations

Unless specifically stated otherwise, as apparent from the discussion above, it is appreciated that throughout the specification discussions utilizing terms such as "processing," "computing," "calculating," "determining," or the like, refer to the action and/or processes of a computer or computing system, or similar electronic computing device, for example comprising processors, that manipulate and/or transform data represented as physical, such as electronic, quantities within the computing system's registers and/or memories into other data similarly represented as physical quantities within the computing system's memories, registers or other such information storage, transmission or display devices.

An embodiment of the invention may be implemented, for example, using a non-transitory computer readable medium or article which may store an instruction or a set of instructions that, if executed by a machine having a processor, cause the processor to perform a method and/or operations in accordance with embodiments of the invention. Such a machine having a processor may include, for example, any suitable processing platform, computing platform, computing device, processing device, computing system, processing system, computer, processor, or the like, and may be implemented using any suitable combination of hardware and/or software. The non-transitory computer readable medium or article may include, for example, any suitable type of memory unit, memory device, memory article, memory medium, storage device, storage article, storage medium and/or storage unit, e.g., memory, removable or non-removable media, erasable or non-erasable media, writeable or re-writeable media, digital or analog media, hard disk, floppy disk, COMPACT DISK READ ONLY MEMORY (CD-ROM), COMPACT DISK RECORDABLE (CD-R), COMPACT DISK REWRITEABLE (CDRW), optical disk, magnetic media, various types of DIGITAL VERSATILE DISKS (DVDs), a tape, a cassette, or the like. The instructions may include any suitable type of code, for example, source code, target code, compiled code, interpreted code, executable code, static code, dynamic code, or the like, and may be implemented using any suitable high-level, low-level, object-oriented, visual, compiled and/or interpreted programming languages like C, C++, JAVA, BASIC, PASCAL, FORTRAN, COBOL, assembly language, machine code, or the like.

The above discussion is meant to be illustrative of the principles and various embodiments of the invention. Numerous variations and modifications will become apparent to those skilled in the art once the above disclosure is fully appreciated. It is intended that the following claims be interpreted to embrace all such variations and modifications.

We claim:

1. A system for performing task execution in a workflow, the system comprising:
a processor device;
at least one modular device comprising a digital microscope that is interchangeably coupled to the processor device;
a memory device coupled to the processor device comprising instructions that when executed by the processor device execute a software service;
a network interface; and
an electronic workflow system coupled to the processor device via the network interface,
wherein,
the digital microscope corresponds to at least one particular task of a workflow to authenticate a workflow item using discrepancy detection, and
the software service controls operation of the at least one modular device and generates forensic metadata from task information received by the digital microscope of the at least one modular device for the electronic workflow system,
the digital microscope facilitates the capture of both intentional printing shapes and unintentional printing artifacts caused by a printing process of the printer and interaction with the ink on a substrate of the workflow item to authenticate the workflow item based on the printing of the workflow item itself.

2. The system of claim 1, wherein the at least one modular device is coupled to a second modular device comprising a sensor device and wherein the at least one and second modular devices transmit data to the software service.

3. The system of claim 1, wherein the at least one modular device is connected to a multifunction printer through either a line or wireless connection.

4. The system of claim 1, wherein the digital microscope comprises a catadioptric or dioptric lens.

5. The system of claim 1, wherein the software service initiates operation of the at least one modular device in response to a reactive workflow command from the electronic workflow system.

6. The system of claim 1, wherein the software service comprises a layered software architecture.

7. The system of claim 6, wherein the layered software architecture comprises a program element in a layer to enable the software service to control operation of the at least one modular device.

8. The system of claim 1, wherein the digital microscope is configured to forensically analyze a given mark in the document to provide a biometric response.

9. A method for electronic workflow system operation, comprising:
sensing information concerning one or more workflow-related tasks with a plurality of modular devices which include at least one digital microscope;
receiving an indication through either a line or wireless connection that a first modular device with the digital microscope of the plurality of modular devices has been connected to a processor device for performing an authentication task related to a workflow using discrepancy detection;
receiving forensic data from the first modular device through either the line or wireless connection concerning the authentication task at a software service executing on the processor device; and
creating forensic metadata from the data received from the first modular device for use in an electronic workflow system coupled to the processor via a network connection,
wherein at least one of the plurality of modular devices is connected to a multifunction printer and wherein the digital microscope facilitates the capture of both intentional printing shapes and unintentional printing artifacts caused by a printing process of the printer and interaction with the ink on a substrate of a workflow item to authenticate the workflow item based on the printing of the workflow item itself.

10. The method of claim 9, wherein, each of the plurality of modular devices couples interchangeably with the processor device.

11. The method of claim 9, further comprising coupling a second modular sensing device of the plurality for performing a second task related to a workflow using the same connection to the processor device used by the first modular device.

12. The method of claim 9, wherein the digital microscope is configured to forensically analyze a given mark in the document to provide a biometric response.

13. A non-transitory computer-readable medium having stored thereon instructions which when executed by a processor cause the processor to perform the method of:
receiving a workflow command from an electronic workflow system coupled to the processor via a network connection to perform an authentication task using discrepancy detection;
mapping the received workflow command into a sequence of forensic data collection tasks to be performed using at least one module device comprising a sensing module with a digital microscope connected to the processor through either a line or wireless connection;
controlling the operation of the at least one module device using a corresponding digital microscope control element through either the line, the wireless connection, or the network connection; and
transmitting forensic data using the network connection concerning the task to the electronic workflow system,
wherein the at least one modular device is connected to a multifunction printer and wherein the digital microscope facilitates the capture of both intentional printing shapes and unintentional printing artifacts caused by a printing process of the printer and interaction with the ink on a substrate of a workflow item to authenticate the workflow item based on the printing of the workflow item itself.

14. The non-transitory computer-readable medium of claim 13, wherein said control element is maintained in a centralized-control server in the network to control a plurality of workflow kiosks.

15. The non-transitory computer-readable medium of claim 14, wherein at least one of the at least one module devices is an interchangeably coupleable sensing module and wherein item-level data is received while controlling the operation of the at least one of the interchangeably coupleable sensing module.

16. The non-transitory computer-readable medium of claim 13, wherein the electronic workflow system comprises a plurality of computer systems within a Web-based computing cloud.

17. The non-transitory computer readable medium of claim 13, wherein the digital microscope is configured to forensically analyze a given mark in the document to provide a biometric response.

* * * * *

UNITED STATES PATENT AND TRADEMARK OFFICE
CERTIFICATE OF CORRECTION

| | | |
|---|---|---|
| PATENT NO. | : 9,176,743 B2 | Page 1 of 1 |
| APPLICATION NO. | : 13/810697 | |
| DATED | : November 3, 2015 | |
| INVENTOR(S) | : Steven J Simske et al. | |

It is certified that error appears in the above-identified patent and that said Letters Patent is hereby corrected as shown below:

In the claims,

In column 26, lines 38 approx., in Claim 17, delete "computer readable" and insert --computer- readable--, therefor.

Signed and Sealed this
Fifth Day of April, 2016

Michelle K. Lee
*Director of the United States Patent and Trademark Office*